(12) United States Patent
Zobele

(10) Patent No.: US 9,192,690 B2
(45) Date of Patent: Nov. 24, 2015

(54) ADJUSTABLE VOLATILE SUBSTANCE DIFFUSER DEVICE WITH A CONTAINER WITH A MEMBRANE

(75) Inventor: Franco Zobele, Trento (IT)

(73) Assignee: Zobele Holding SPA, Trento (IT)

( * ) Notice: Subject to any disclaimer, the term of this patent is extended or adjusted under 35 U.S.C. 154(b) by 2076 days.

(21) Appl. No.: 12/294,214

(22) PCT Filed: Mar. 24, 2006

(86) PCT No.: PCT/EP2006/002716
§ 371 (c)(1),
(2), (4) Date: Jun. 9, 2009

(87) PCT Pub. No.: WO2007/110086
PCT Pub. Date: Oct. 4, 2007

(65) Prior Publication Data
US 2009/0302128 A1    Dec. 10, 2009

(51) Int. Cl.
*A61L 9/12* (2006.01)
*A01M 1/20* (2006.01)

(52) U.S. Cl.
CPC ................ *A61L 9/12* (2013.01); *A01M 1/2044* (2013.01); *A61L 2209/15* (2013.01)

(58) Field of Classification Search
CPC ........................................................ A61L 9/12
USPC .................. 239/34, 53, 55, 56, 57, 58, 59, 60
See application file for complete search history.

(56) References Cited

U.S. PATENT DOCUMENTS

| | | | |
|---|---|---|---|
| 4,157,787 A | | 6/1979 | Schwartz |
| 4,279,373 A | * | 7/1981 | Montealegre .................. 206/0.5 |
| 4,280,651 A | * | 7/1981 | Montealegre et al. ........ 229/122 |
| 4,523,870 A | * | 6/1985 | Spector .......................... 454/157 |
| 4,849,606 A | * | 7/1989 | Martens et al. ................ 392/390 |
| 5,115,975 A | | 5/1992 | Shilling |
| 5,167,877 A | | 12/1992 | Pai |
| 5,178,327 A | * | 1/1993 | Palamand et al. ................ 239/57 |
| 5,518,790 A | | 5/1996 | Huber et al. |
| 6,085,989 A | * | 7/2000 | Cox ................................ 239/59 |
| 2005/0127538 A1 | | 6/2005 | Fabrega et al. |

FOREIGN PATENT DOCUMENTS

| | | |
|---|---|---|
| DE | 3223780 A1 | 3/1983 |
| EP | 1319543 A1 | 6/2003 |
| EP | 1479400 A1 | 11/2004 |
| EP | 1698355 A1 | 9/2006 |
| WO | 9742983 A1 | 11/1997 |

* cited by examiner

*Primary Examiner* — Ryan Reis
(74) *Attorney, Agent, or Firm* — Albert Bordas, P.A.

(57) ABSTRACT

The present invention refers to adjustable volatile substance diffuser devices, more specifically to diffusers incorporating a container with a semipermeable membrane (3, 23, 43, 63). Said membrane (3, 23, 43, 63) permits the issue of vapors but prevents the escape of liquids, with the result that an extremely clean device is achieved as the spillage of liquid is prevented in the case of inappropriate handling. The device (1, 21, 41, 61) is furthermore of very simple construction, as it is made up of two parts, a container (2, 22, 42, 62) which houses the volatile substance and a housing (4, 24, 44, 64), which supports said container (2, 22, 42, 62). The container (2, 22, 42, 62) has the membrane (3, 23, 43, 63) adhered to it. The container (2, 22, 42, 62) and the housing (4, 24, 44, 64) are coupled directly to each other and they are moved by means of guiding or articulation. The container (2, 22, 42, 62) may comprise a useful part (16), which defines the cavity (5) holding the volatile substance, and a non-useful part (6).

40 Claims, 19 Drawing Sheets

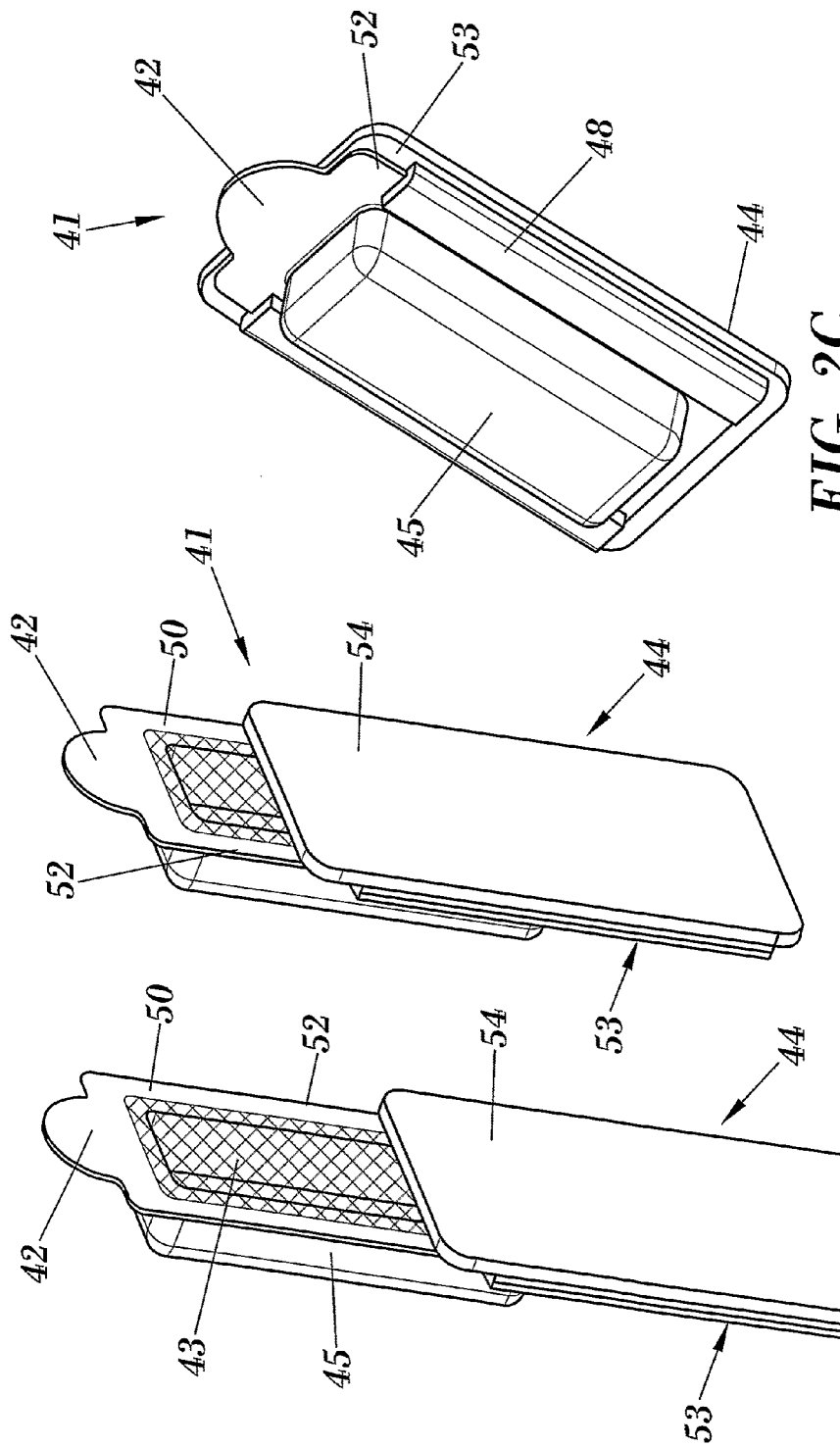

ADJUSTABLE VOLATILE SUBSTANCE DIFFUSER DEVICE WITH A CONTAINER WITH A MEMBRANE

OBJECT OF THE INVENTION

The present invention is related to the regulation of volatile substance diffuser devices. More specifically, the present invention is related to volatile substance diffusers incorporating a container with a semipermeable membrane. Said semipermeable membrane permits the outlet of vapours but stops liquids from escaping, so that an extremely clean device is thereby achieved, as it prevents liquid being spilled in the event of improper handling.

The diffuser device of the present invention is notable for its simplicity, both of manufacture and of assembly, for its small size, and for its easy handling, as it achieves the regulation of the degree of evaporation of the volatile substance by means of just two parts.

The device is specially designed for use in conjunction with a stream of air so as to boost thereby the evaporation and diffusion of the volatile substance. This stream of air may be natural, like that generated as a result of the movement of people, opening of doors or windows, etc. or else forced. The interior ventilation outlet of a vehicle is an example of a stream of forced air.

BACKGROUND TO THE INVENTION

Volatile substance diffuser systems incorporating semipermeable membranes that permit the outlet of vapours but impede the escape of liquids are already known. These systems are based on a container, which consists of a heat-formed portion and a membrane. As the membrane is flat, the formed portion is designed with a flat circumferential lip where the heat-formed portion and the membrane are welded together. The heat-formed portion is designed so that it may contain the sufficient amount of liquid.

These systems are notable for being both economical and clean, as they prevent liquid being spilled in the event of improper handling.

No type of additional housing is included in their simplest applications, such as for instance in U.S. Pat. Nos. 4,157,787 and 5,518,790.

In other cases, this container is presented inside a usually plastic housing, which acts both as a protection and as a support. The housing also contributes to a better presentation of the product. As an example of systems with housings we may mention U.S. Pat. No. 4,849,606.

International patent application WO 2005/056063 A1 and European patent application EP 1319543 A1 describe one of these latter volatile substance diffuser systems. Thus, these documents describe a plastic housing which also has the function of regulating the system. For this purpose, the housing has an added element that is movable in relation to the housing, which performs the function of regulating the substance evaporated by means of partly or fully closing openings situated at the back of the housing.

These systems, however, have a series of drawbacks, which are explained below. On the one hand, the moving part which is added to the housing represents an extra cost, both in terms of a larger number of parts and of assembly. On the other hand, although the sealing of the openings is total, since there is a gap left between the membrane and the back of the housing, the device may go on evaporating, so that an inactive state of the system is never achieved.

DESCRIPTION OF THE INVENTION

The present invention endeavours to resolve the problems stemming from the earlier volatile substance diffuser systems by means of a device that is notable for its simplicity of manufacture and assembly, its small size, and its easy handling, as the evaporator device of the present invention successfully regulates the degree of evaporation of the volatile substance by means of just two parts: the housing and the container, which has a semipermeable membrane stuck or adhered to it. The container and the membrane therefore form an air freshener unit. In addition, since the gap between the membrane and the inner part of the housing is reduced to a minimum, the device achieves an optimum regulation of the volatile substance.

One of the aspects of the present invention refers to a volatile substance evaporator device by means of a semipermeable membrane with an adjustable degree of evaporation, where the air flow participates in the evaporation of a volatile substance, which comprises a container that houses in a cavity a volatile substance, a semipermeable membrane adhered to one face of the container and at least partly in contact with the volatile substance housed in said cavity, and a housing in which the container, on its face closed by the semipermeable membrane, and the housing are designed to be coupled directly, i.e. without the need for the intervention of any other element. During the use of the device, on its face closed by the semipermeable membrane, the container and the housing are coupled to each other directly, either entirely or partly, on the same plane and they are movable in relation to each other, so that the degree of evaporation of the volatile substance is regulated by means of the relative movement between the housing and the container. In other words, the relative movement between the housing and the container acts as a regulating element.

The device that is the object of the present invention, therefore, does not require any additional regulating or protective element during its use to carry out the regulation of the degree of evaporation of the volatile substance housed inside the container and in contact with the semipermeable membrane.

In its minimum configuration, the housing has an outer and an inner wall.

The volatile substance, preferably in liquid or solid state or else in gel form, consists of an air freshener product and/or insecticide or the like.

The semipermeable membrane is adhered or stuck to the peripheral lip of the container, forming an airtight seal, while said peripheral lip of the container and the semipermeable membrane are welded together.

The volatile substance is enclosed in the assembly. In one possible embodiment, the connection between the housing and the container is stable, in which case the device will be single use, i.e. for use and disposal. In another possible embodiment, these parts are removable to permit the fitting of a new container filled with volatile substance.

In addition, the volatile substance evaporator device may have guiding means that permit the relative movement between the housing and the container on the same plane.

The volatile substance evaporator device may also have means of articulation that permit the relative movement between the housing and the container. These means of articulation permit rotation around a pin of one element in relation to the other, on the same plane.

In both cases (with guiding means or articulation means), the degree of the evaporation of said volatile substance may be determined by the amount of surface area of the housing that is directly coupled to or overlapping a certain amount of semipermeable membrane, said degree of evaporation being minimum when the whole of the surface area of the semipermeable membrane is concealed or hidden by the wall of the housing and maximum when the semipermeable membrane is not covered by the wall of the housing at all, that is to say, when the semipermeable membrane is entirely unconcealed or uncovered. This simply means that, during the relative movement between the housing and the container, the face of the container that has the semipermeable membrane adhered to it gradually moves away from the wall of the housing on which said face of the container is coupled, so that the amount of surface area of the container and of the housing, which remain entirely coupled to or overlapping each other, may be adjusted.

On the other hand, it is possible that during the relative movement between the housing and the container the whole of the surface area of the wall of the housing may be kept entirely coupled to, superimposed on or overlapping the whole of the surface area of the container on the same plane. In this case, the housing has one or more holes or openings that communicate the outer wall of the housing with the inner wall of the housing, facilitating the evaporation of said volatile substance. The degree of the evaporation of the volatile substance is regulated according to the greater or lesser extent to which the semipermeable membrane adhered to the container is aligned with said hole or holes.

In addition, the dimensions of the housing wall may be similar to those of the semipermeable membrane or they may be substantially greater than those of the semipermeable membrane.

Furthermore, on its face closed by the semipermeable membrane, the container may comprise a useful part in contact with the volatile substance and a non-useful part isolated from the volatile substance, the extent of the evaporation of said volatile substance being regulated according to whether the opening(s) or holes are aligned partly or fully with said non-useful part of the face of the container. This part is "non-useful" because it is fully isolated from the volatile substance, which is housed in a cavity defined by the "useful" part. That is to say, the "non-useful" part has no contact with the contents of the cavity containing the volatile substance, irrespective of the amount of said substance that is contained in said cavity, and irrespective also of the position in which the container is placed.

Optionally, other lesser guiding means may be added to the housing, preferably in the form of a circumference arc, but with a radius smaller than that of the above-described guiding means.

In addition, the useful part may comprise two receptacles, chambers or cavities joined to one another by a third receptacle, cavity or chamber situated in the central portion of the container. On its outer side this third receptacle comprises a protuberance or lesser receptacle of smaller size than the rest of said third receptacle, so that the rotation of this protuberance brings about the guiding movement of the container in relation to the housing. This protuberance or lesser receptacle is capped at the top end by its last element, which may be solid (i.e. not house volatile substance) or hollow (i.e. houses volatile substance). This last element, preferably smaller sized than the protuberance from which it stems, may be a die, a cylinder, a button, a cone, a nut or any other equivalent or similar element.

In addition, said non-useful part of the container may take on the form of a laminar surface, i.e. a flat surface, the semipermeable membrane being fully welded on said non-useful part in the form of a laminar surface of the face of the container.

Optionally, said non-useful part of the container may define a second cavity completely separate from the cavity where the volatile substance is housed, said separation being achieved by means of a weld zone between the semipermeable membrane and the container.

Optionally, said non-useful part of the container may comprise a hole.

It is also possible for the container to be movable in respect of the housing, which remains fixed, or for the housing to be movable in respect of the container, which remains fixed.

In addition, the semipermeable membrane may fit completely snug to the inner wall of the housing when the container and the housing are entirely or partly coupled, or it may be substantially separate from said inner wall.

In a preferred embodiment the housing is made in a single piece and more specifically, it is a rigid plastic material structure produced by means of injection moulding, although no other material or procedure for making the housing is ruled out.

The device may comprise means of attachment, for instance to a fixed structure such as the air outlet grille of a ventilation system of a vehicle or any ventilation grille situated in any open or closed environment. The device is thus immersed in the stream of air generated. These means of attachment are situated on the fixed part of the device, namely on the housing or on the container, depending on the embodiment.

DESCRIPTION OF THE DRAWINGS

To supplement the description that is being given and in order to assist in a clearer understanding of the features of the invention, in accordance with various preferential examples of practical embodiments of same, this description is accompanied as an integral part hereof by a set of drawings, wherein there is represented, for informative and non-restrictive purposes, the following:

FIGS. 2A, 2B and 2C show other front and side (FIGS. 2A and 2B) and rear and side (FIG. 2C) perspective views of the device according to a version of the same embodiment.

In FIGS. 8B and 8E, the non-useful part of the container partly covers the holes in the housing. Finally, in FIG. 8C the non-useful part of the container does not cover the holes in the housing at all, but its useful part covers them entirely.

In FIG. 14B, the non-useful part of the container partly covers the holes in the housing. Finally, in FIG. 14C the non-useful part of the container does not cover the holes in the housing at all, but its useful part covers them entirely.

PREFERRED EMBODIMENTS OF THE INVENTION

Figures 1A, 1B:
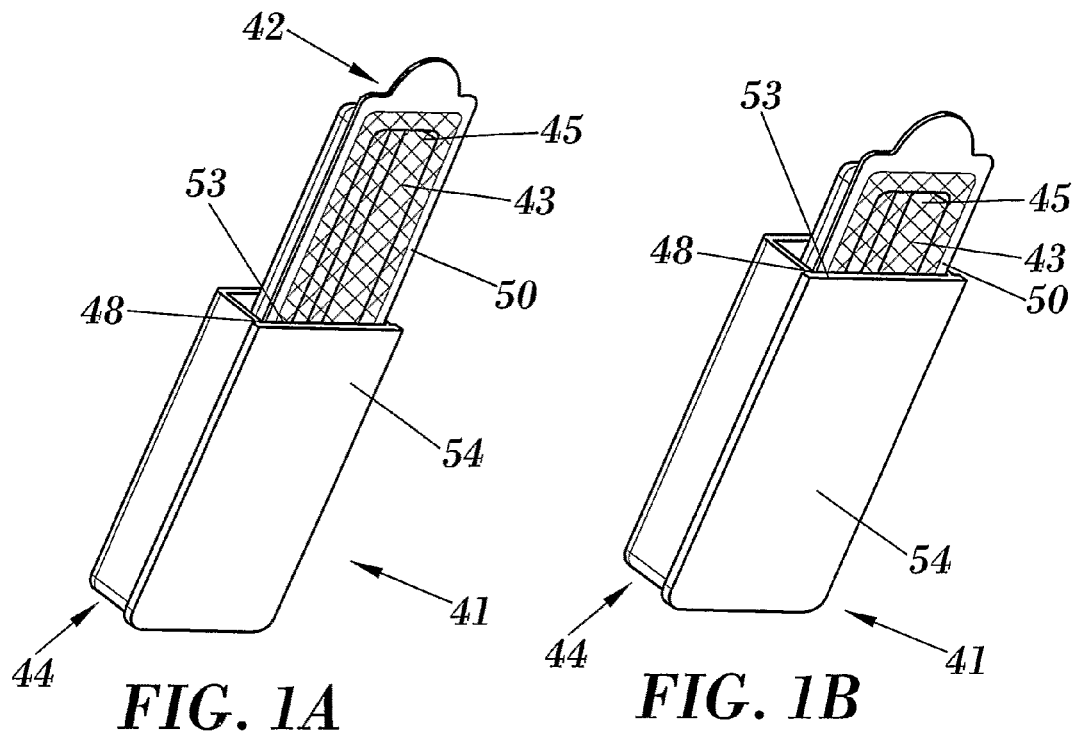
FIGS. 1A, 1B and 1C show front and side perspective views of the device of a first embodiment of the present invention.
Figure 1C:
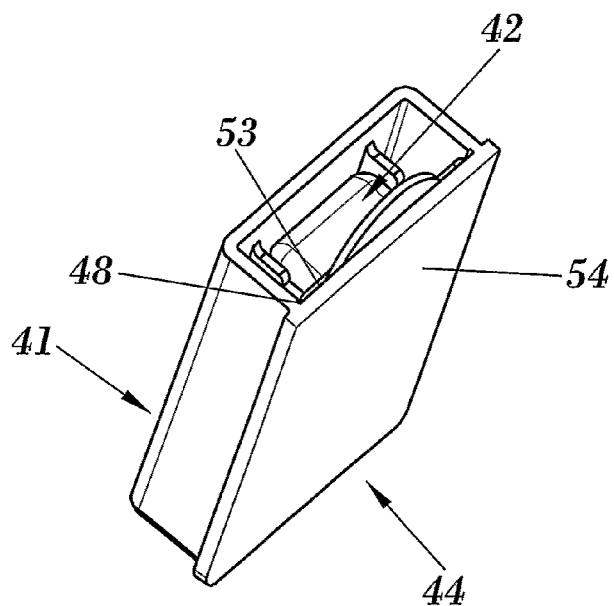

In the light of FIGS. 1A to 1C, it may be observed that in one of the preferred embodiments of the invention, the evaporator device (41) comprises a container (42) housing in a cavity (45) a volatile substance to be evaporated, which is preferably in a liquid state, but it may also be, for instance, in a solid state or in gel form. The container (42) is hermetically sealed by a semipermeable evaporation membrane (43), so that the volatile substance is in direct contact with a larger portion of the inner surface of the membrane (43), which is impermeable to liquids, so that no spillage is possible. The membrane (43) is, however, permeable to vapour, so that it permits the evaporation of the liquid retained.

In a particular embodiment of the present invention, the container (42) may take the form of a cone, cup, die or any other shape of those familiar to experts on the matter.

In a particular embodiment of the present invention, the container (42) is made by heat-forming a plastic material such as, for instance, PET, PP or PVC, but no other material or procedure for manufacturing the container is discounted.

The housing (44) takes on a configuration or shape that may in general be any one, for instance circular, rectangular, or any other. FIGS. 1A, 1B and 1C show a housing (44) able to hold the container (42), i.e. the container (42) may be inserted in the housing (44).

Alternatively, the housing (44) may take on a minimal configuration such that it is formed of a wall that has an outer surface (54) and an inner surface (53). This is shown in FIGS. 2A, 2B and 2C.

In a preferred embodiment, said housing (44) is rigid.

As may be observed, the device for the diffusion of volatile substances (41) via a semipermeable membrane does not require an intermediate part to couple the container (42) to the housing (44), rather the container (42) and the housing (44) are coupled to each other directly. The fact of the housing (44) and the container (42) being coupled directly to the semipermeable membrane (43) adhered or stuck to said container (42) makes for simplicity in its use and handling and, in particular, it permits optimum adjustment of the evaporation of the volatile substance.

On its face (50) closed by the semipermeable membrane (43), the container (42) and the inner wall (53) of the housing (44) are attachable—they are designed to be coupled—to each other directly and entirely and they are movable in relation to each other on the same plane, the relative position between both being what determines the degree of evaporation of the volatile substance. The inner wall (53) of the housing (44) is, therefore, substantially flat.

In other words, during its use the device that is the object of the present invention does not need any additional regulating or protective element in order to effect the adjustment of the degree of evaporation of the volatile substance housed inside the container (42) and in contact with the semipermeable membrane (43).

The outer surface of the semipermeable membrane (43) is provided with a protection strip that prevents the evaporation of the volatile substance prior to use of the device. This protection strip is easily detachable and extends partly from the device (41), forming a tab that facilitates its removal at the time of using the device. This protection strip is not shown in the figures.

This protection strip plays no part in the regulation of the evaporation of the volatile substance when the device is being used. It merely prevents the volatile substance from evaporating before the device is used by the consumer. In fact, the regulation provided by the device (41) does not start until said protection strip has been detached.

The relative movement between the housing (44) and the container (42) may be achieved as the container (42) is movable in respect of the housing (44), which remains fixed.

Said relative movement may also be achieved since the housing (44) is movable in respect of the container (42), which remains fixed.

In addition, the semipermeable membrane (43) may be adjusted snugly to the wall (53) of the housing (44) when the container (42) and the housing (44) are entirely or partly coupled, or it may also be substantially separate from the wall (53) of the housing (44) when the container (42) and the housing (44) are entirely or partly coupled.

In the preferred embodiments illustrated by FIGS. 1A, 1B, 1C, 2A, 2B and 2C, the volatile substance evaporator device (41) is provided with guiding means (48) that permit the relative movement between the housing (44) and the container (42).

As may be observed in FIG. 2C, the guiding means (48) are two parallel grooves established along the wall (53) of the housing (44). Alternatively, said parallel grooves may be joined at their lower end so that a U-shaped guide is established, said lower end acting as a brake or bottom stop for the container. To guide the container (42) along said parallel grooves, the container (42) has a peripheral lip (53) for engagement in said parallel grooves in the housing (44). Other guiding means (48) are also possible.

In this case, the degree of evaporation of the volatile substance is determined by the amount of the surface area of the housing (44) that is directly coupled to a certain amount of the surface area of the container (42) and, therefore, of semipermeable membrane (43), said degree of evaporation being minimum when the whole of the surface area of the semipermeable membrane (43) is hidden or concealed by the wall (53) of the housing (44) (FIGS. 1C and 2C) and maximum when the semipermeable membrane (43) is entirely uncovered or unconcealed by the wall (53) of the housing (44) (FIGS. 1A and 2A).

FIGS. 1A, 1B, 1C, 2A, 2B and 2C show a housing (44) in which the form of the inner wall (53), which is the one that is coupled to or overlaps the container (42)—which has the semipermeable membrane (43) adhered to it—is rectangular or square, but other different shapes are also possible. In these figures, the form of the surface area of the container (42) to which the semipermeable membrane (43) is adhered is also square or rectangular, but likewise other different shapes are also possible.

In this embodiment of the invention, the dimensions of the inner wall (53) of the housing (44), i.e. its width and height, are similar to the dimensions of the semipermeable membrane (43), as well as to those of the surface area of the container (42) to which the semipermeable membrane (43) is adhered.

FIGS. 3A, 3B, 3C and 3D show a second preferred embodiment of the present invention, in which the volatile substance evaporator device (61) is also provided with guiding means (68) that permit relative movement between the housing (64) and the container (62). These guiding means are similar to those used in the previous case (FIGS. 1A, 1B, 1C, 2A, 2B and 2C).

In the light of FIGS. 3A, 3B, 3C and 3D, the evaporator device (61) also comprises a container (62) that houses in a cavity (65) a volatile substance to be evaporated, which is preferably in a liquid state, but may also be, for instance, in a solid state or in gel form. The container (62) is hermetically sealed by a semipermeable evaporation membrane (63) (which is not shown in the figures), so that the volatile substance is in direct contact with a larger portion of the inner surface of the membrane (63), which is impermeable to liquids, so that no spillage is possible. The membrane (63) is, however, permeable to vapour, so that it permits the evaporation of the liquid retained.

FIGS. 3A, 3B, 3C and 3D show a housing (64) in which the form of the inner wall (73), which is the one that is coupled to or overlaps the container (62)—which has the semipermeable membrane (43) adhered to it—is rectangular or square and has rounded corners, but other different shapes are also possible. In these figures, the form of the surface area of the container (62) to which the semipermeable membrane (63) is adhered is also square or rectangular with rounded corners, but likewise other different shapes are also possible. The inner wall (73) of the housing (64) is substantially flat.

In this embodiment of the invention, the overall height of the inner wall (73) of the housing (64) is substantially or considerably larger than the height of the cavity (65) which houses the volatile substance.

In addition, in this possible embodiment, the housing (64) has one or more holes or openings (67) communicating the outer wall (74) of the housing (64) with the inner wall (73) of said housing (64), which facilitate the evaporation of said volatile substance, the degree of evaporation of the volatile substance being regulated according to the extent to which the semipermeable membrane (63) adhered to the container (62) is aligned with said holes or openings (67). In the event of the housing (64) having several holes, these are grouped in at least one selected area of said housing (64).

Figure 3A:
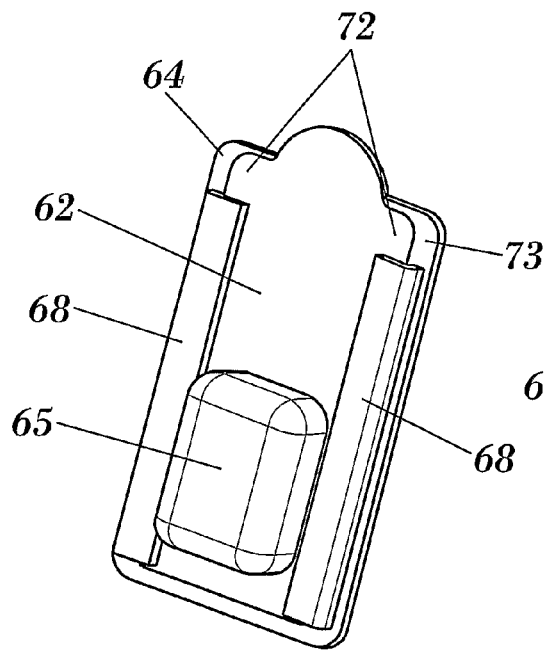
FIGS. 3A, 3B, 3C and 3D show rear and side (FIG. 3A) and front and side (FIGS. 3B, 3C and 3D) perspective views of the device of a second embodiment of the present invention.
Figure 3B:
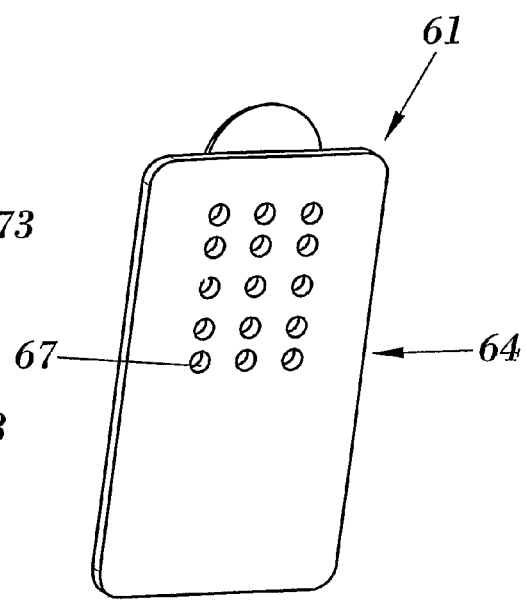
Figure 3C:
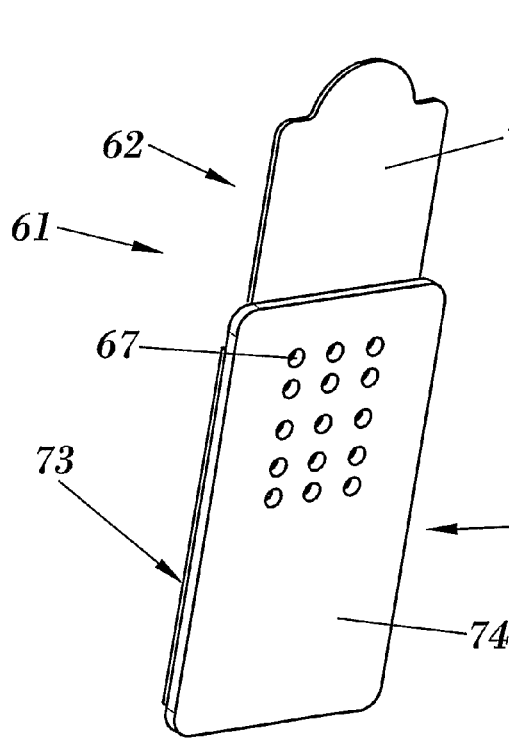
Figure 3D:
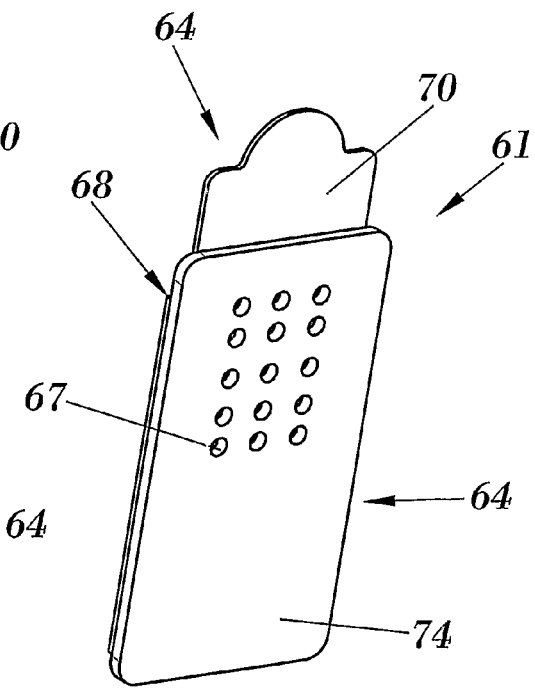

As may be observed in FIG. 3A, the guiding means (68) are two parallel grooves established along the wall (73) of the housing (64). Alternatively, said parallel grooves may be joined at their lower end so that a U-shaped guide is established, said lower end acting as a brake or bottom stop for the container (62). To guide the container (62) along said parallel grooves, the container (62) has a peripheral lip (72) for engagement in said parallel grooves in the housing (64). Other guiding means (68) are also possible.

Figure 4A:
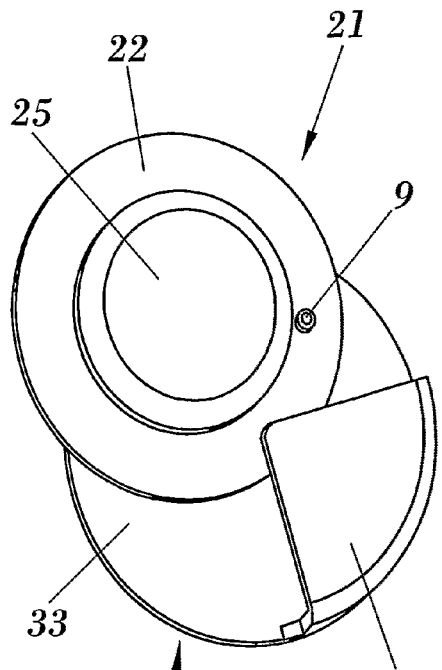
FIGS. 4A, 4B and 4C show front and side (FIGS. 4A and 4C) and rear and side (FIG. 4B) perspective views of the device of a third embodiment of the present invention.
Figure 4B:
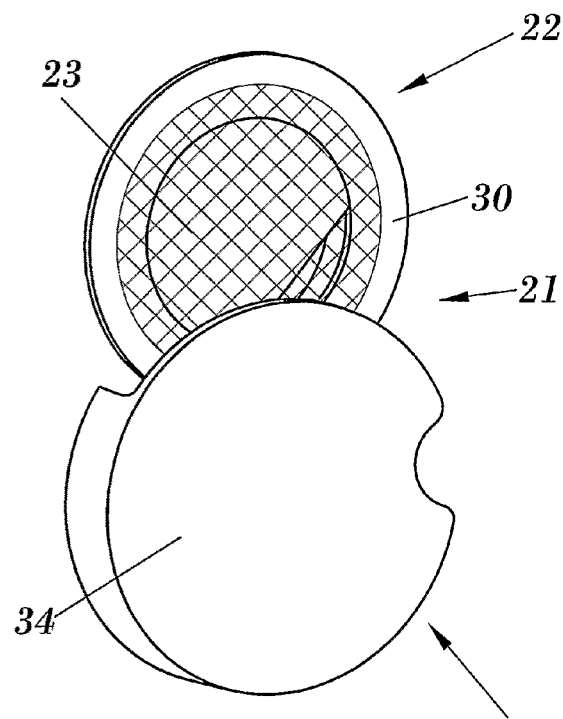
Figure 4C:
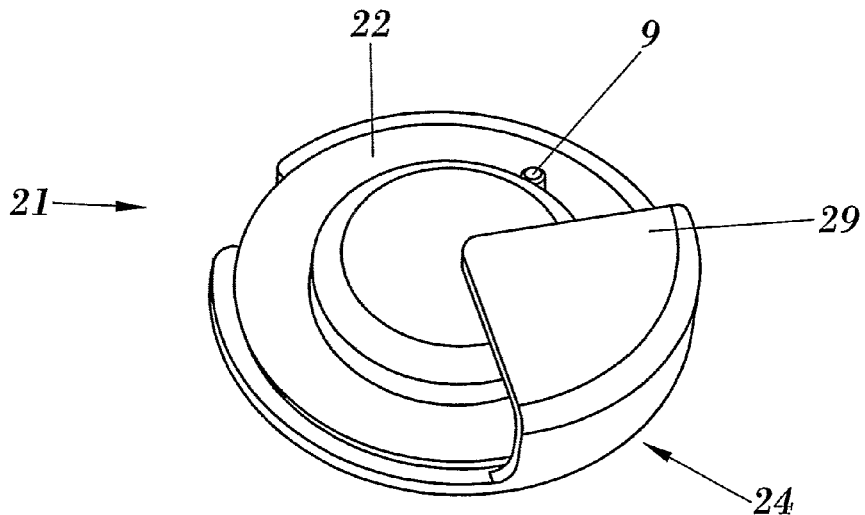

FIGS. 4A, 4B and 4C show a third preferred embodiment of the present invention, in which the volatile substance evaporator device (21) is provided with articulating or articulation means (9) that permit the relative movement between the housing (24) and the container (22) on the same plane. These articulation means permit rotation around a pin of one element in respect of the other.

In the light of FIGS. 4A, 4B, and 4C, the evaporator device (21) comprises a container (22) that houses in a cavity (25) a volatile substance to be evaporated, which is preferably in a liquid state, but it may also be, for instance, in a solid state or in gel form. The container (22) is hermetically sealed by a semipermeable evaporation membrane (23), so that the volatile substance is in direct contact with a larger portion of the inner surface of the membrane (23), which is impermeable to liquids, so that no spillage is possible. The membrane (23) is, however, permeable to vapour, so that it permits the evaporation of the liquid retained.

In this case, the degree of evaporation of the volatile substance is determined by the amount of the surface area of the housing (24) that is directly coupled to or superimposed on a certain amount of the surface area of the container (22), said degree of evaporation being minimum when the whole of the surface area of the semipermeable membrane (23) is hidden or concealed by the inner wall (23) of the housing (24) (FIG. 4C) and maximum when the semipermeable membrane (23) is entirely uncovered or unconcealed by the inner wall (23) of the housing (24) (FIG. 4B). The inner wall (33) of the housing (24) is, therefore, substantially flat.

FIGS. 4A, 4B and 4C show a housing (24) in which the form of the inner wall (33), which is the one that is coupled to or overlaps the container (22), is circular, but other different shapes such as square, rectangular or others are also possible. In these figures, the form of the surface area of the container (22) to which the semipermeable membrane (23) is adhered is also circular, but likewise other different shapes are also possible.

FIGS. 4A, 4B and 4C show that the housing (24) incorporates a flange or wedge (29) in the form of a circular sector which partly surrounds the container (22). The function of this flange may be to protect the device, to facilitate its handling, to contribute to its support during the articulated movement of the container (22) in respect of the housing (24), and/or merely for questions of appearance.

FIGS. 5 to 9 show a fourth preferred embodiment of the present invention, in which the volatile substance evaporator device (1) is provided with guiding means (8) that permit the relative movement between the housing (2) and the container (4).

Figure 6A:
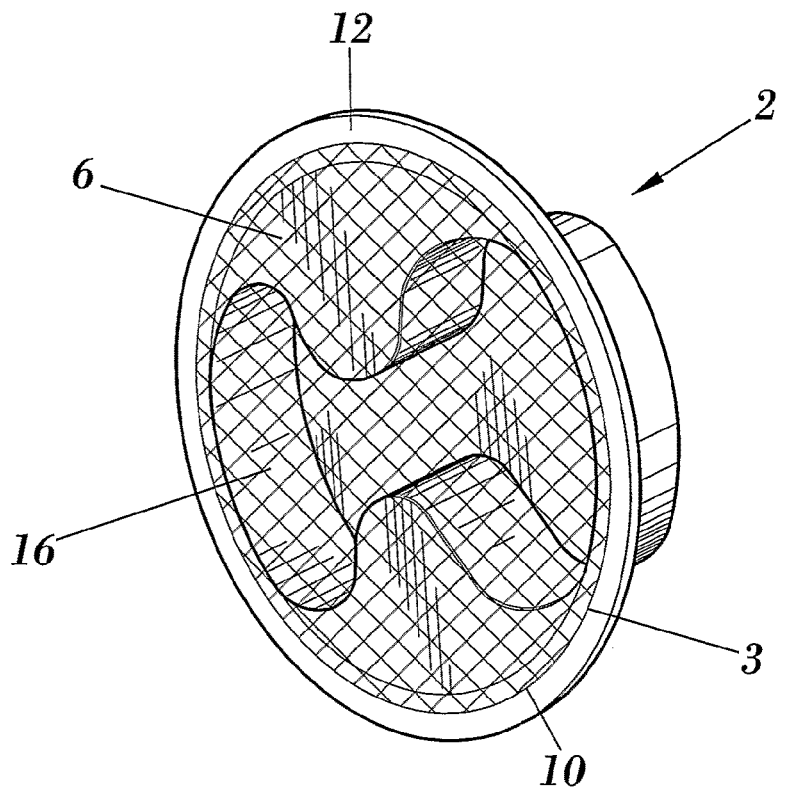
FIGS. 6A, 6B, 6C and 6D show different views of the container, according to the fourth embodiment of the present invention.
Figure 6B:
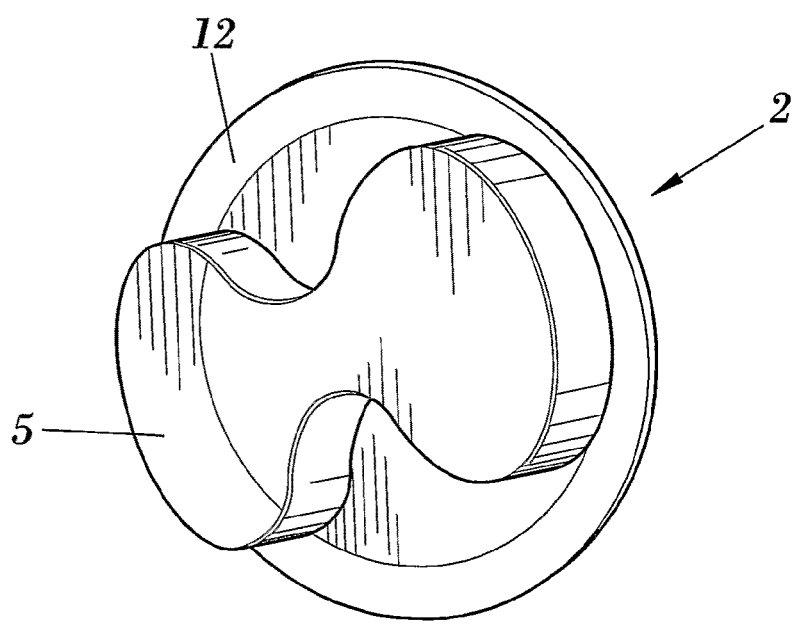
Figure 6C:
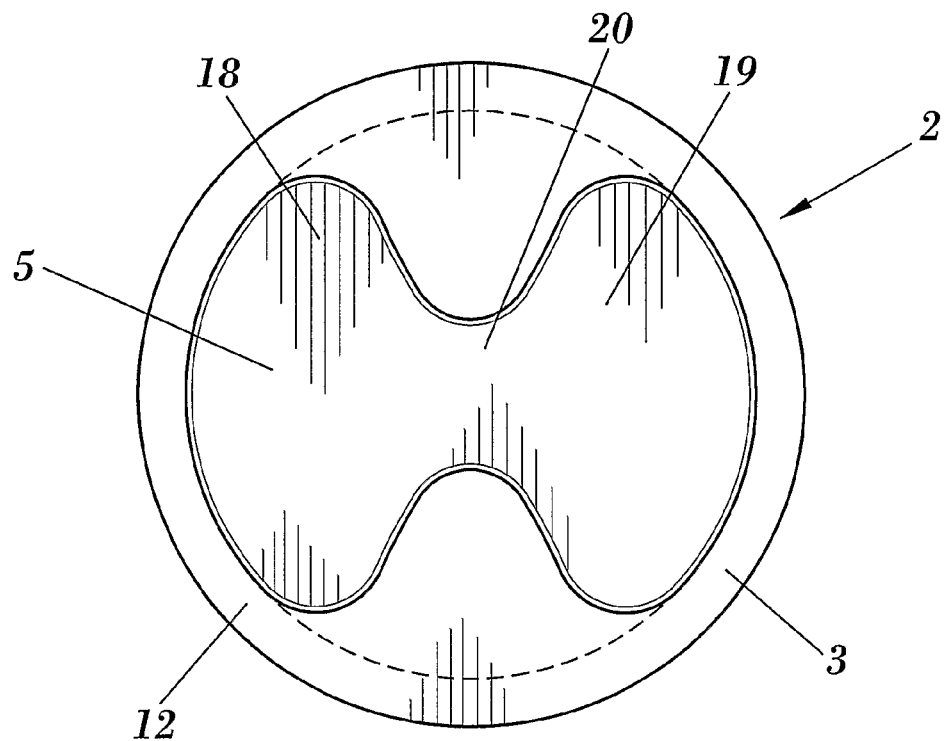
Figure 6D:
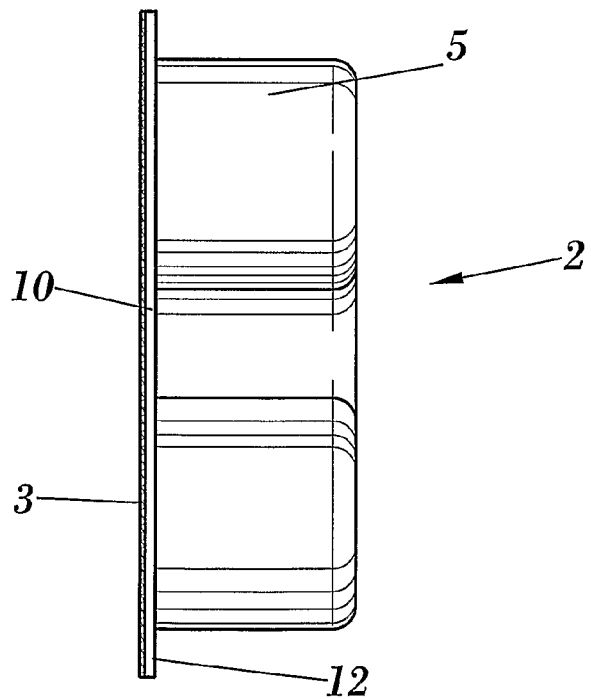

In the light of FIGS. 6A, 6B, 6C and 6D, it may be observed that the evaporator device (1) comprises a container (2) that houses in a cavity (5) a volatile substance to be evaporated, which is preferably in a liquid state, but it may also be, for instance, in a solid state or in gel form. The container (2) is hermetically sealed by a semipermeable evaporation membrane (3), as is shown in FIGS. 6A and 6D, so that the volatile substance is in direct contact with the larger portion of the inner surface of the membrane (3), which is impermeable to liquids, so that no spillage is possible. The membrane (3) is, however, permeable to vapour, so that it permits the evaporation of the liquid retained.

As may be observed in FIGS. 5 to 8, the degree of the evaporation of the volatile substance is not determined by the amount of surface area of the housing (4) (represented in FIGS. 7A, 7B, 7C and 7D) which is directly superimposed on or coupled to a certain amount of surface area of the container (2), rather during the relative movement between the housing (4) and the container (2) the whole of the surface of the inner wall (13) of the housing (4) is kept entirely coupled to, superimposed on or overlapping on the same plane the whole of the surface area of the container (2) and, therefore, of the semipermeable membrane (3) adhered to the container (2). The inner wall (13) of the housing (4) is, therefore, substantially flat.

FIGS. 8A, 8B, 8C, 8D, 8E and 8F show an example of this embodiment. In this example the coupling surface between the housing (4) and the container (2) is circular. This form facilitates the guiding between both elements. However, no form is excluded that permits the guiding between the containers (2) and the housing (4).

Figure 7A:
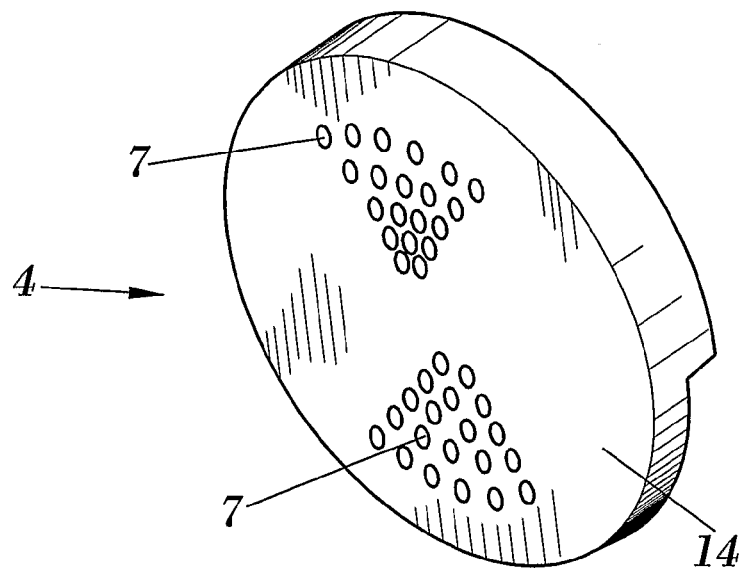
FIGS. 7A, 7B, 7C and 7D show different views of the housing, according to the fourth embodiment of the present invention.
Figure 7B:
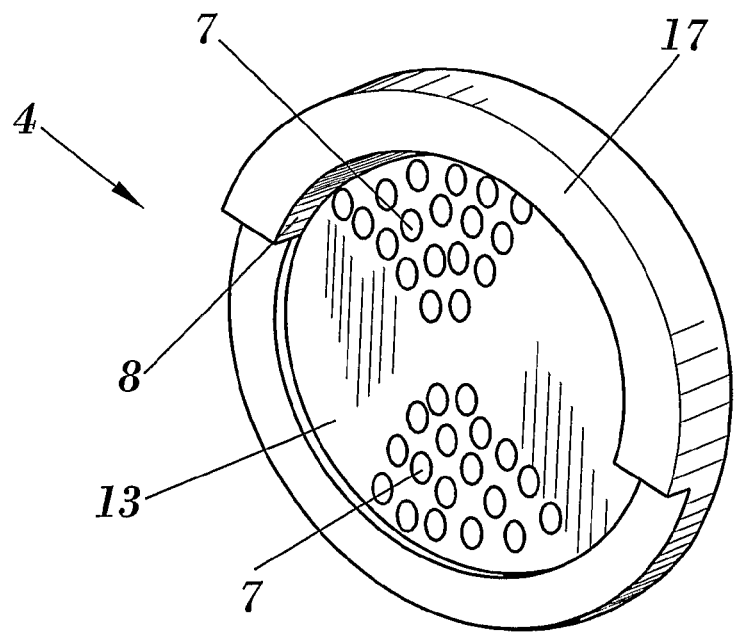
Figure 7C:
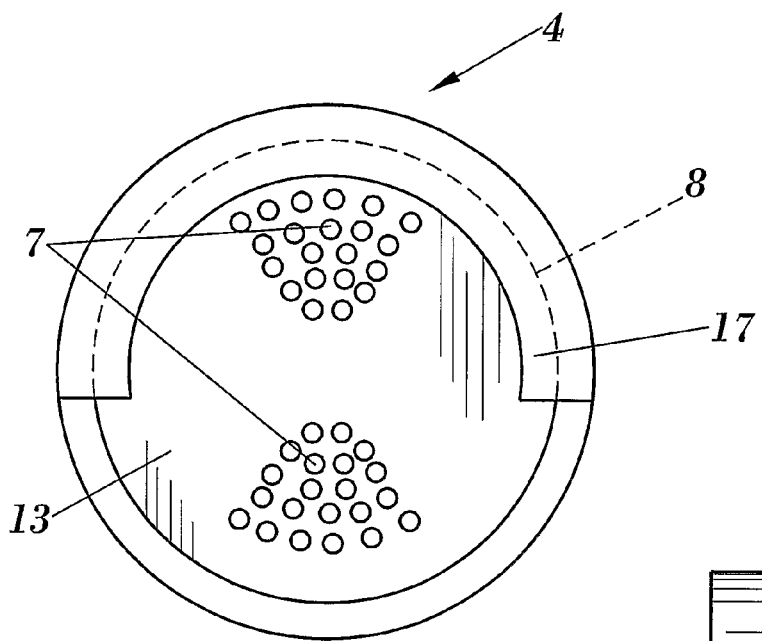
Figure 7D:
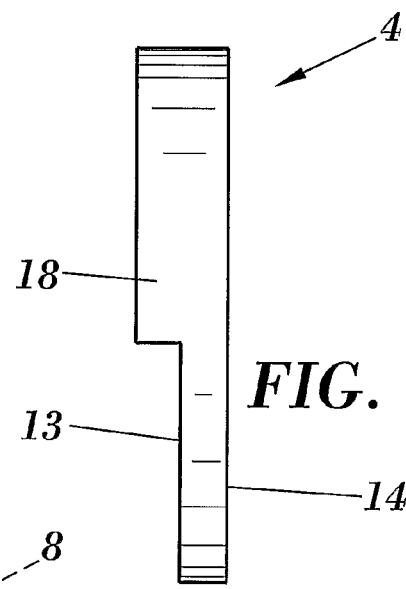

In this example illustrated by FIGS. 7A, 7B, 7C, 7D, 8A, 8B, 8C, 8D, 8E and 8F, in which the coupling surface between the housing (4) and the container (2) has a circular form, the guide or guiding means (8) are situated on the housing (4). The guide (8) forms a groove established in the perimeter of the housing (4), in the form of a circumference arc (17), which, as shown in FIG. 7C, forms a semicircumference, although said arc (17) does not necessarily have to occupy a semicircumference, rather the arc (17) may be larger or smaller. To guide the container (2) along said groove in the perimeter of the housing (4), the container has, as shown in FIGS. 6A, 6B, 6C, 6D, 8A, 8B, 8C, 8D, 8E and 8F, a peripheral lip (12) for engaging with said perimeter arc of the housing (4).

In addition, in this possible embodiment of the invention, the housing (4) has at least one hole or opening (7) that communicates or communicate the outer wall (14) of the housing (4) with the inner wall (13) of said housing (4), which facilitates or facilitate the evaporation of said volatile substance, the degree of the evaporation of the volatile substance being regulated according to the greater or lesser extent to which the semipermeable membrane (3) adhered to the container (2) is aligned with said hole or holes (7). This is shown in FIGS. 8A, 8B, 8C, 8D, 8E and 8F. If the housing (4) has various holes or openings (7), these are grouped into at least one selected area of the housing (4) and the device may be designed so that the openings or holes (7) are grouped in various selected areas of the housing (4). This is shown in FIGS. 7A, 7B and 7C, in which the holes or openings (7) are grouped in two selected areas of the housing. In this case the two areas, each of which has one group of openings or holes (7), are opposed in respect of the centreline dividing the housing into two semicircumferences, but said groups of holes or openings (7) may be arranged in a different way in the housing (4). The holes or openings (7) may also be slots.

Figure 5A:
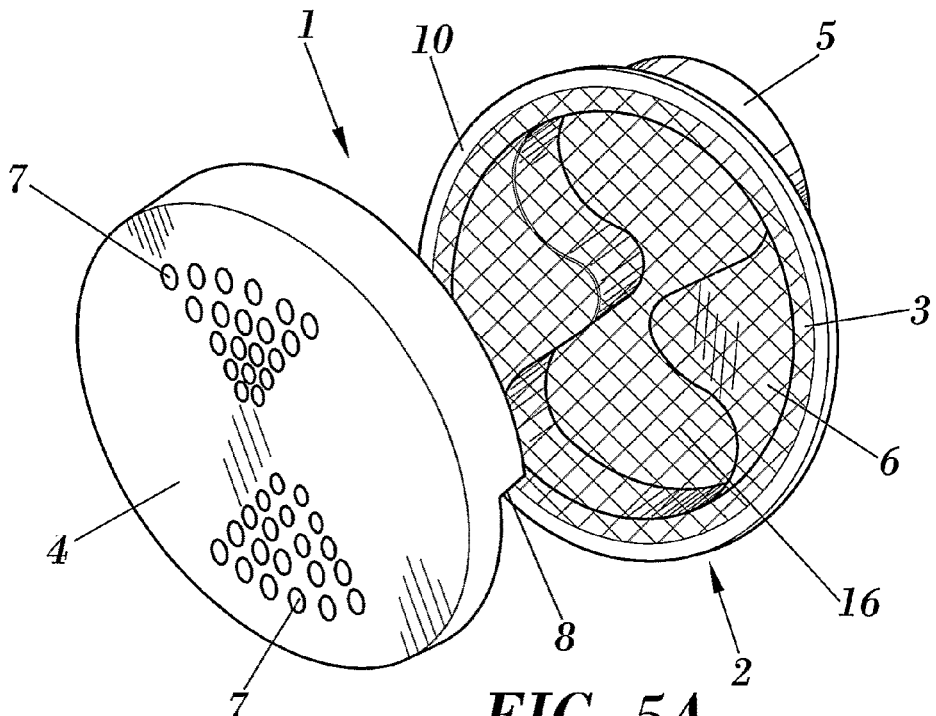
FIGS. 5A and 5B show a rear and side (FIG. 5A) and front and side (FIG. 5B) perspective of an exploded view of the parts making up the device of a fourth embodiment of the present invention.
Figure 5B:
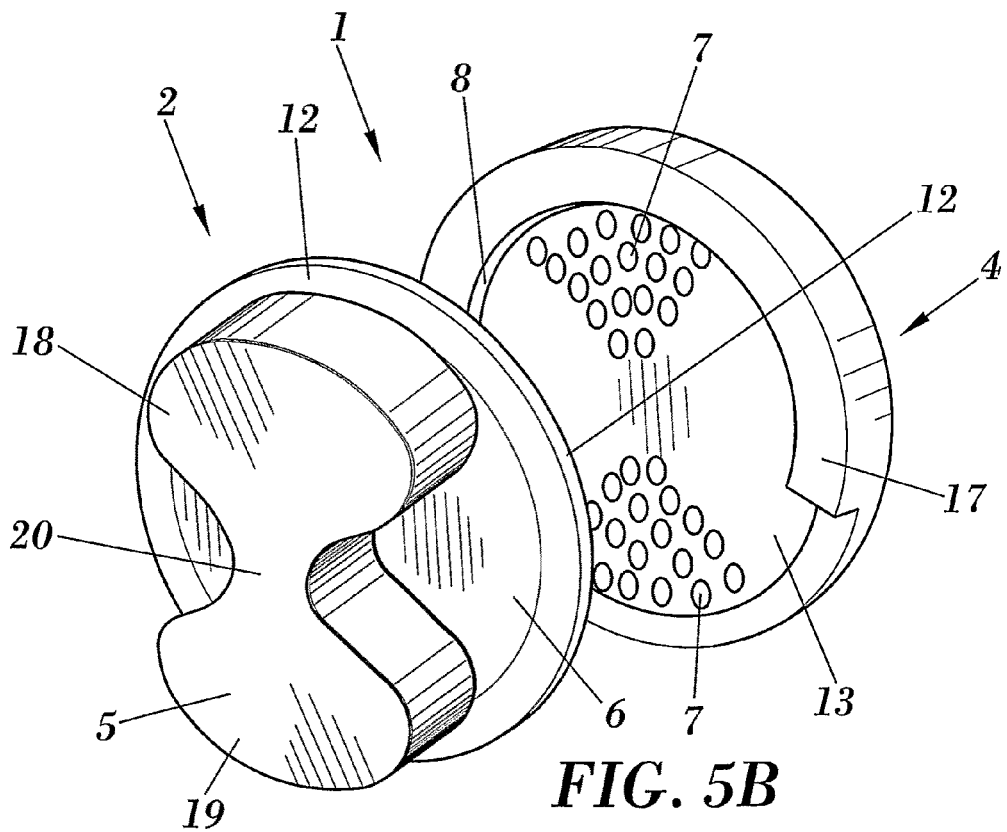

As may be observed in FIGS. 5A and 6A, on its face (10) closed by the semipermeable membrane (3), the container (2) comprises a useful part (16) in contact with the volatile substance and a non-useful part (6) isolated from the volatile substance, the extent of the evaporation of said volatile substance being regulated according to whether the opening or hole or openings or holes (7) in the housing (4) are aligned partly or fully with said non-useful part (6) of the face (10) of the container (2). In other words, the extent of the evaporation of the volatile substance is regulated according to whether openings or holes (7) in the housing (4) are aligned partly or entirely with said useful part (16) in contact with the volatile substance.

The holes or openings (7) in the housing (4) may be made by the methods familiar to experts on the matter. If the housing (4) has a single hole or opening (7), this may adopt a larger diameter than that of the case of various holes in order to permit good adjustment of the evaporation of volatile substance in the case of maximum regulation.

Figure 8A:
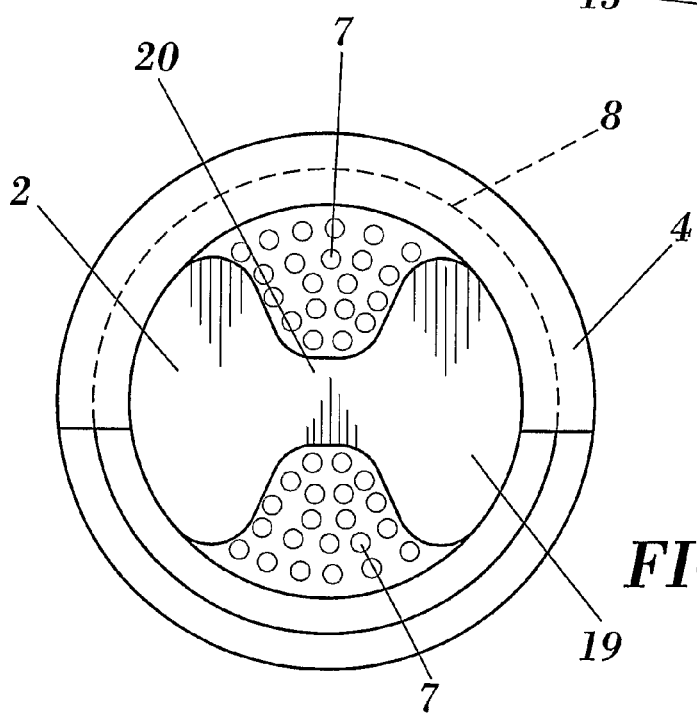
FIGS. 8A, 8B, 8C, 8D and 8E show views in different positions of the use of the device according to the fourth embodiment of the present invention. Thus, in FIGS. 8A and 8D, the non-useful part of the container fully covers the holes in the housing.
Figure 8B:
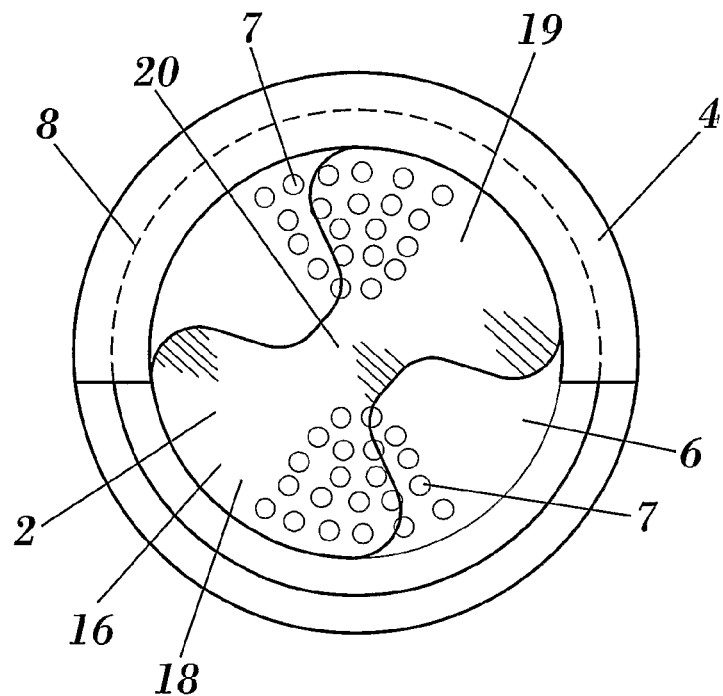
Figure 8C:
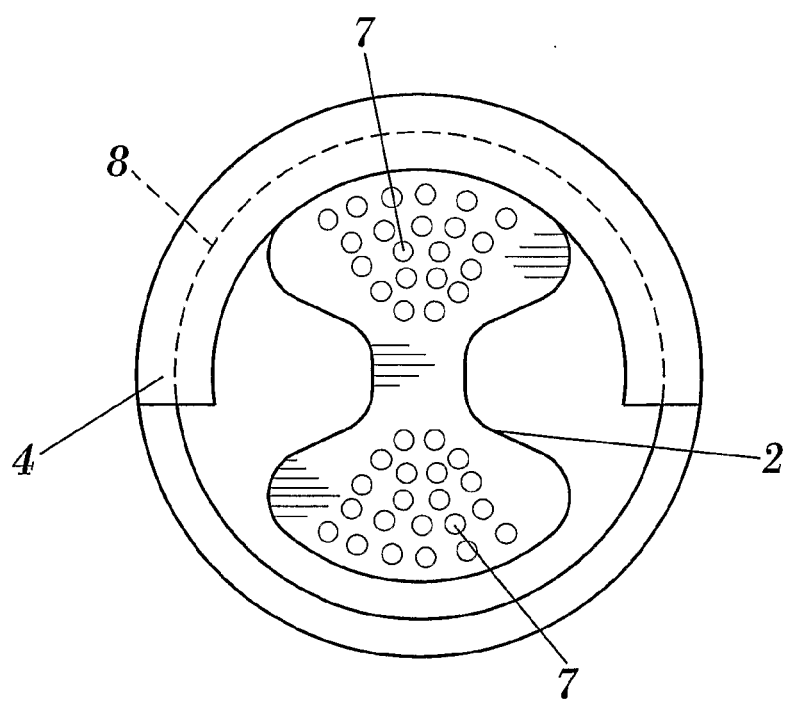
Figure 8D:
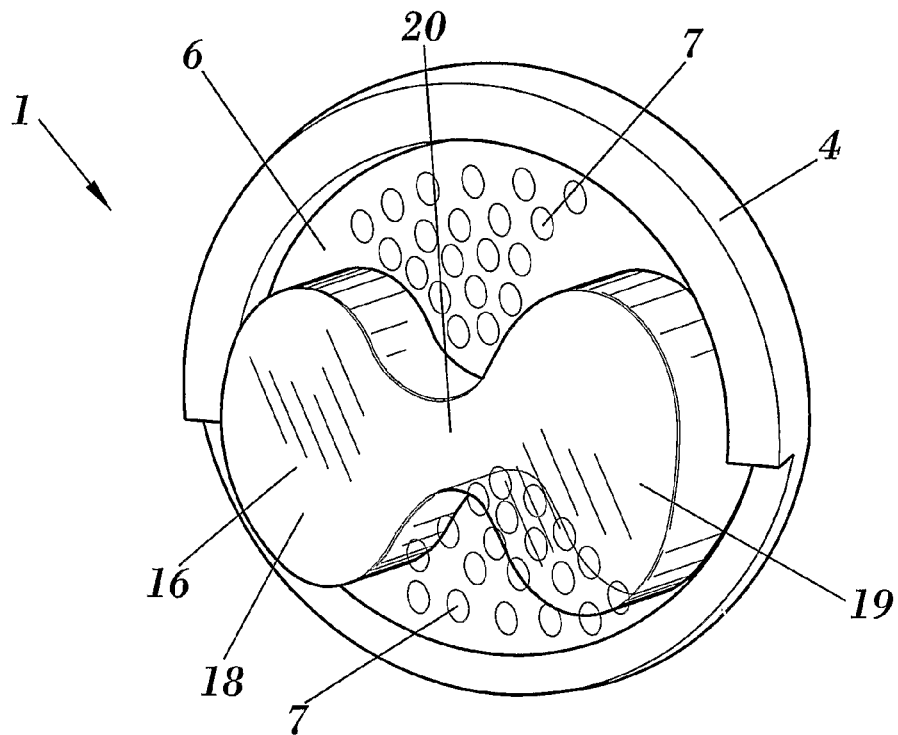

Thus, in FIGS. 8A and 8D, the non-useful part (6) of the container (2) entirely covers the holes (7) in the housing (4), so that the semipermeable membrane (3) is not in contact with the volatile substance housed in the useful part (16) of the container (2).

Figure 8E:
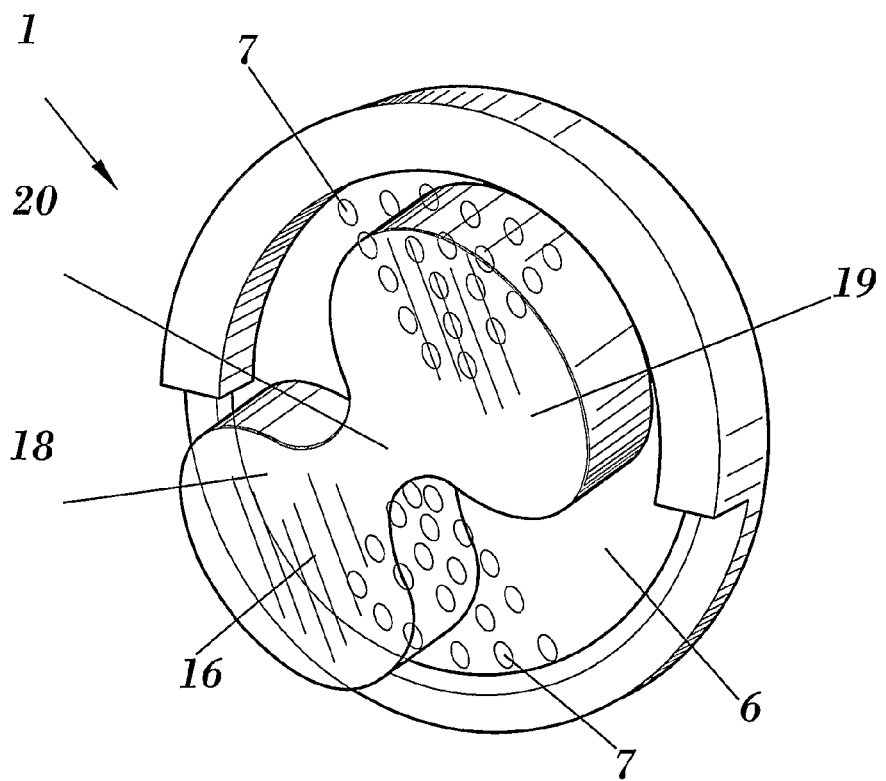

In FIGS. 8B and 8E, the non-useful part (6) of the container (2) partly covers the holes (7) in the housing (4), so part of the semipermeable membrane (3) is in contact with the volatile substance housed in the useful part (16) of the container (2) and part of said semipermeable membrane (3) is not in contact with the volatile substance housed in the useful part (16) of the container.

Lastly, in FIG. 8C, the non-useful part (6) of the container (2) does not cover the holes (7) in the housing (4) at all, but its useful part (16) covers them entirely. Therefore, the degree of the evaporation of the volatile substance is maximum in this case.

Put in another way, the container (2) comprises a laminar surface (6) from which there extends a cavity (5) that contains the volatile substance and whose inner surface is in contact with the semipermeable membrane (3), with the result that between said laminar surface (6) and the part of the semipermeable membrane (3) adhered to said laminar surface (6), there is no volatile substance, the degree of the evaporation of said volatile substance housed in the cavity (5) in the container (2) being regulated according to whether the openings or holes (7) in the housing (4) are aligned partly or entirely with said laminar surface (6) of the container (2).

In other words, the container (2) may have part of its projected surface of substantially no depth (6), with the result that between said part of the container (2) of projected surface of substantially no depth (6) and the semipermeable membrane (3), there is no amount of volatile substance, the degree of the evaporation of said volatile substance housed in the part of the container (2) of projected surface of a certain depth, i.e. in the cavity (5) which contains the volatile substance, being regulated according to whether the openings or holes (7) in the housing (4) are aligned partly or entirely with the part of the container (2) of substantially no depth (6) or with the part of the container (2) which has a certain depth (5).

Or what amounts to the same, the surface that defines the container (2) is extended towards the face (10) of said container (2) to which the semipermeable membrane (3) is adhered, said extended surface (6) establishing a plane parallel to the one occupied by the semipermeable membrane (3), with the result that between said extended surface (6) of the container (2) and the part of the semipermeable membrane (3) adhered to said part (6) of the container (2), the amount of volatile substance is substantially nil, while the extent of the evaporation of said volatile substance housed in the cavity (5) in the container (2) is regulated according to whether the openings or holes (7) in the housing (4) are aligned partly or entirely with said extended surface (6) of the container (2).

In addition, the non-useful part (6) of the face (10) of the container (2) may take on the form of a laminar surface, i.e. of a flat surface.

Thus, the part of the semipermeable membrane (3) which is adhered to the non-useful part (6) in the form of a laminar surface of the face (10) of the container (2) may be fully welded to said non-useful part (6) in the form of a laminar surface of the face (10) of the container (2).

Alternatively, the non-useful part (6) of the face (10) of the container (2) may define a second cavity completely separate from the cavity (5)—defined by the useful part (16)—where the volatile substance is housed, so that said separation is achieved by means of a weld zone between the semipermeable membrane (3) and the container (2). This cavity without liquid or volatile substance may have a cosmetic or mechanical function. For example, it may be used as a guiding element or as a bearing point for rotation. This possibility is not shown in the figures accompanying the present description.

Alternatively too, the non-useful part (6) of the face (10) of the container (2) consists of a hole, i.e. the non-useful part (6) may be fully or partly die-stamped. Thus, a weight reduction is achieved and the device is lightened. The hole may also be used as a guide or as a bearing point for turning the housing in respect of the container or vice versa. This possibility is not illustrated either in the figures accompanying the present description.

FIGS. 8A, 8B, 8C, 8D, 8E and 8F show an example wherein the face (10) of the container (2) which has the semipermeable membrane (3) adhered to it comprises a useful part (16) in contact with the volatile substance, defining this useful part (16) the cavity (5) that houses the volatile substance, and a non-useful part (6) isolated from the volatile substance, the degree of the evaporation of said volatile substance being regulated according to whether the openings or holes (7) in the housing (4) are aligned partly or entirely with said non-useful part (6) of the face (10) of the container (2). In this example, the cavity (5) of the container (2) defined by the useful part (16) is made up of two receptacles, chambers or cavities (18, 19) linked by a narrower chamber, cavity or receptacle (20). This may be seen, for instance, in FIGS. 5B, 6C and 8B. The non-useful part (6) successfully reduces or prevents evaporation entirely depending on whether said non-useful part (6) is aligned partly or entirely—respectively—with one or more holes (7) made in the housing (4).

As we may have observed, the device of this embodiment is designed so that, in this case, the useful part (16) that defines two chambers or cavities (18, 19) has substantially the same surface as the areas of the housing (4) chosen to design the two groups of holes or openings (7), and regulation of the evaporation of the volatile substance is thereby optimized.

Figures 9A, 9B, 9C:
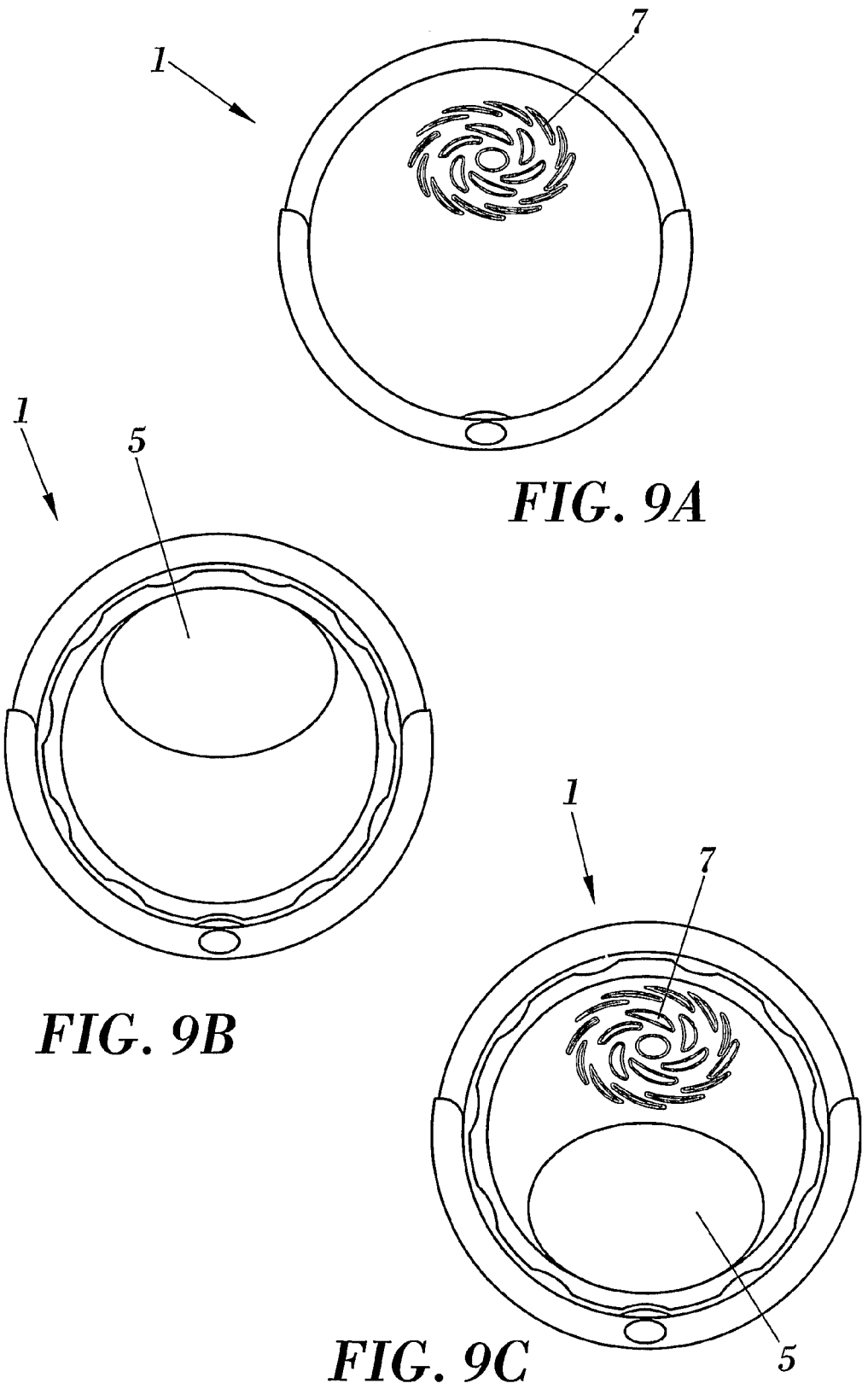
FIGS. 9A, 9B and 9C show views of the device, according to a version of the fourth embodiment of the present invention.

FIGS. 9A, 9B and 9C show another example of the fourth embodiment of the present invention, wherein the cavity (5) of the container (2) defined by the useful part is made up of a single chamber or cavity (5) containing the volatile substance. The non-useful part (6) successfully reduces or prevents entirely evaporation, depending on whether said non-useful part is aligned partly or entirely—respectively—with one or more holes (7) made in the housing (4). In this case, the useful part, which here defines a single chamber or cavity (5), has substantially the same surface area as the area of the housing chosen to design, in this case, the single group of holes or openings (7), and regulation of the evaporation of the volatile substance is thereby optimized.

As an alternative to this fourth embodiment, the non-useful part (6) of the container (2) encompasses or comprises only the perimeter of the useful part (16), said non-useful part (6) forming a flat lip on which the semipermeable membrane (3) and the container (2) are connected or joint. This joint between the semipermeable membrane (3) and the container (2) on this flat peripheral lip is preferably welded. In this case, the surface area of the face (10) closed by the semipermeable membrane (3) is substantially smaller than the surface area of the inner wall (13) of the housing (4), as the rest of the non-useful part (6) has been trimmed or die-stamped, i.e. it has been removed, limiting said non-useful part (6) to the minimum necessary (said peripheral lip) to join or weld the semipermeable membrane (3). In this case, the useful part (16) may also define one or more cavities or receptacles.

Preferably, both parts, the useful (6) and the non-useful (16), of the container (2) form a single structure, preferably of plastic material, which may be PET, PP, PVC or others.

FIGS. 7B and 7C show that the housing (4) is provided with a guide or guiding means (8), in general, so as to facilitate the turning movement of the container (2) relative to that of the housing (4). According to this possible embodiment of the invention, for the use of the evaporator device (1) the housing (4) remains fixed, while the user operates the container (2), which would be the moving part or the one to be turned or shifted.

As already explained, in FIGS. 8A, 8B, 8C, 8D, 8E and 8F it may be seen that the relative movement between the housing (4) and the container (2) has the effect that the holes (7) are superimposed to a greater or lesser extent on the non-useful part (6), also referred to as the projected surface with no depth (6), and thereby the through-area is opened or closed to the flow of air received by the device from the outer surface (14) of the housing (4).

The volatile substance is enclosed in the assembly, as may be seen in the figures. The afore-mentioned joint between the housing (4) and the container (2) is a possible stable embodiment, in which case the device (1) will be single use, i.e. for use and disposal. In another possible embodiment the device is detachable, that is to say, its parts are removable or can be taken apart to permit the fitting in the device of a new container (2) filled with volatile substance.

FIGS. 7A, 7B and 7C show that the housing (4) is preferably provided with one or more holes or openings (7) which communicate its outer wall (14) with the inner one (13). Alternatively, the housing (4) may have air flow slots or openings. Alternatively too, the housing may have a single hole or opening whose size is limited by the perimeter which would restrict it to a cluster of small openings or holes. Put in another way, the area of the housing which had been selected in order to situate a cluster of holes or openings may be perforated entirely, in such a way that one large perforation or hole is left.

Although it has been described that the movement is rotary on guiding means, in another possible embodiment it may also be displacement, by modifying the physical configuration of the container (2) and the housing (4) slightly.

In addition, the guiding means may be situated both on the container (2) and on the housing (4).

In the case of guided movement where the guiding means are designed on the housing (4), the guiding means (8) may have a width greater than the width of the non-useful part (6) isolated from the volatile substance of the container (2). In addition, there may be a space between the guide (8) and the inner surface (13) of the housing (4), as it may be appropriate to leave said space for safety reasons and to prevent damage to the membrane (3) due to rubbing against the inner surface (13) of the housing (4). In any case, this space is very small. In addition, the existence of this space impedes the flow of air through this area.

In the event of its being the container (2) the one that incorporates the guiding means (8), the turning of the housing (4) takes place in respect of the container (2).

If the device is designed so that there is a space between the guide (8) and the inner surface (13) of the housing (4) or so that the guide (8) may be wider than the element to be guided, we avoid possible breakage of the membrane due to contact with possible imperfections of the housing, as may be the case of burrs, which may be due to the movement or to the pressure that is exerted on the device.

FIGS. 5 to 8 show a housing (4) whose coupling surface to the membrane (3) is circular and a container (2) in the form of a figure eight or a sand clock, i.e. made up of two cavities (18, 19) joined together by means of a small cavity or narrower channel (20). However, other forms or different arrangements are also possible, like that of FIGS. 9A, 9B and 9C, or other different arrangements.

FIGS. 6A, 6B, 6C and 6D show how the container (2), especially its cavity or cavities housing the volatile substance, adopts a form that makes for easy handling.

In a preferred embodiment, the housing (4) is made of a single piece, which is preferably a plastic material structure, and more preferably a rigid plastic material produced by injection moulding, but any other material or procedure for making the housing is not discounted.

FIGS. 11 to 14 show a fifth preferred embodiment of the present invention, where the same numbering has been maintained as in the fourth embodiment in order to refer to all those elements which are similar to those of said fourth embodiment. Different numbers have only been used to refer to elements that differentiate this fifth preferred embodiment from the fourth one.

Thus, FIGS. 11 to 14 show a volatile substance evaporator device (1) with a semipermeable membrane (3) which is also provided with guiding means (8) that permit relative movement between the housing (2) and the container (4).

As in the previous embodiment, during the relative movement between the housing (4) and the container (2) the whole of the surface area of the inner wall (13) of the housing (4) is kept entirely coupled to, superimposed on, or overlapping on the same plane the whole of the surface area of the container (2) and, therefore, of the semipermeable membrane (3) adhered or stuck to the container (2). The inner wall (13) of the housing (4) is therefore substantially flat.

Figure 11A:
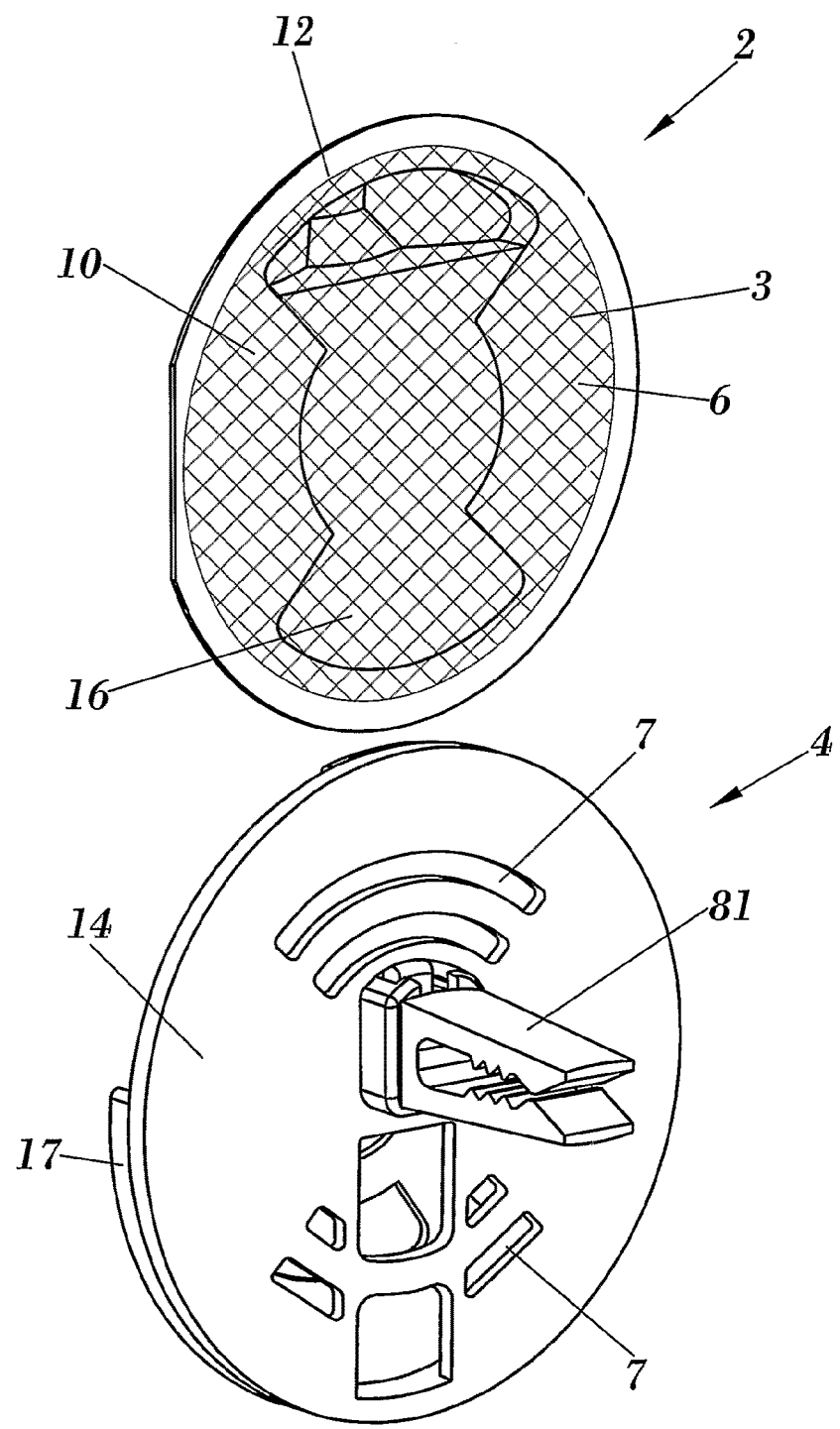
FIGS. 11A and 11B show a rear and side (FIG. 11A) and front and side (FIG. 11B) perspective of an exploded view of the parts making up the device of a fifth embodiment of the present invention.
Figure 11B:
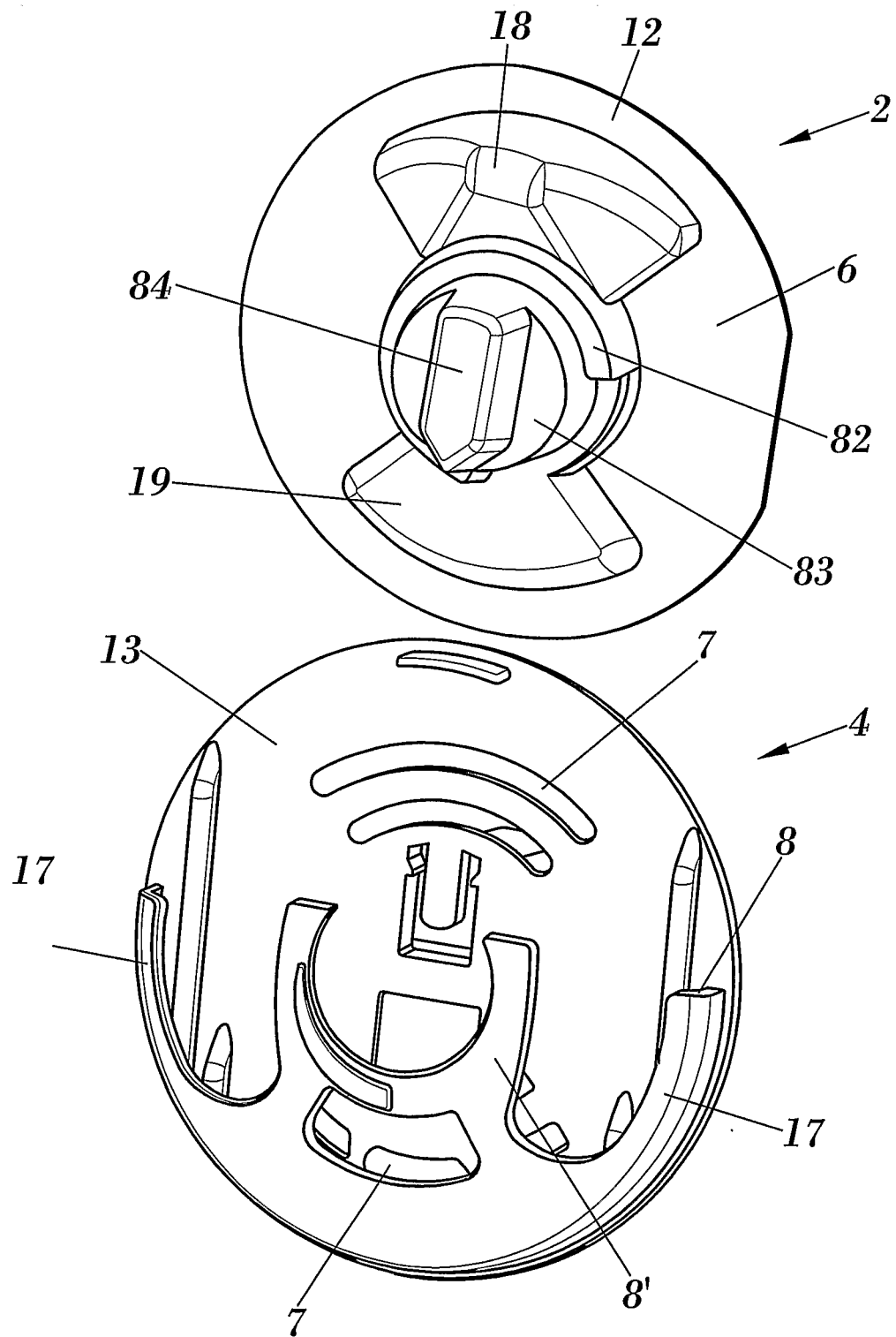

In this example illustrated by FIGS. 11A and 11B, where the coupling surface between the housing (4) and the container (2) has a circular form, the guide or guiding means (8) are situated on the housing (4). As in the fourth embodiment, the guiding means (8) form a groove in the perimeter of the housing (4), in the form of a circumference arc (17), which, as shown in FIG. 13B, forms a semicircumference, although said arc (17) does not necessarily have to occupy a semicircumference, rather the arc (17) may be larger or smaller. To guide the container (2) along said groove in the perimeter of the housing (4), the container has, as shown in FIGS. 12A and 12B, a peripheral lip (12) for engaging with said perimeter arc of the housing (4).

As shown in FIG. 13B, in this preferred embodiment other guiding means (8') are added on the housing (4), preferably in the form of a circumference arc, but with a smaller radius than that of the guiding means (8) described in the previous paragraph. In other words, these guiding means (8') are not situated on the perimeter of the housing (4), but in the central area of said housing (4), and they contribute or work together with the peripheral guiding means (8) in the guiding of the container (2). It is also possible for these non-peripheral guiding means (8'), i.e. those situated in the central area of the housing (4), to be the only guiding means for the device (1), so that the incorporation of guiding means (8) situated on the perimeter of the housing (4) is not necessary.

Figure 13A:
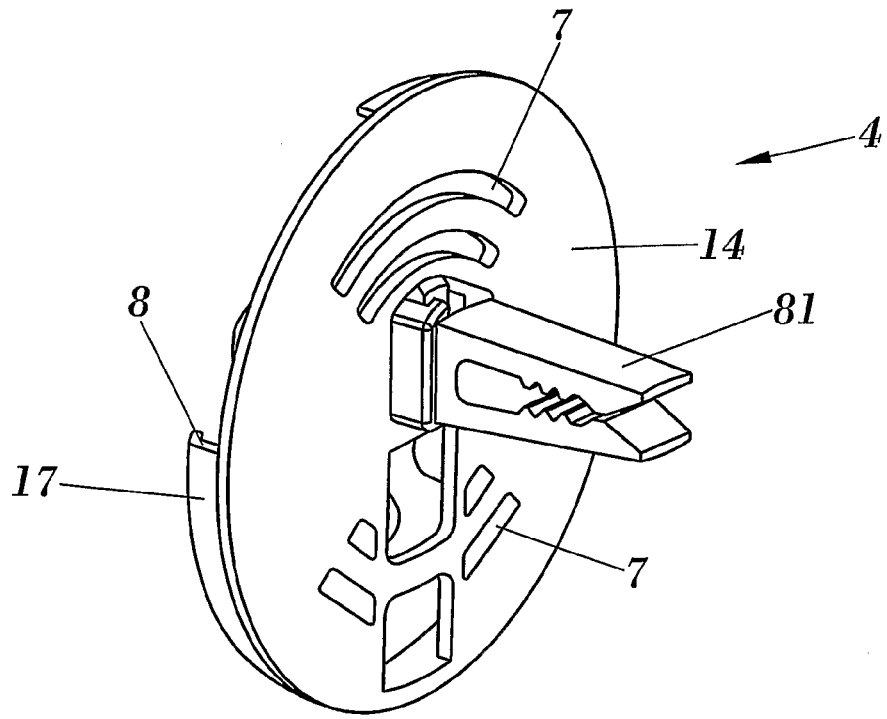
FIGS. 13A and 13B show rear and front views of the housing, according to the fifth embodiment of the present invention.
Figure 13B:
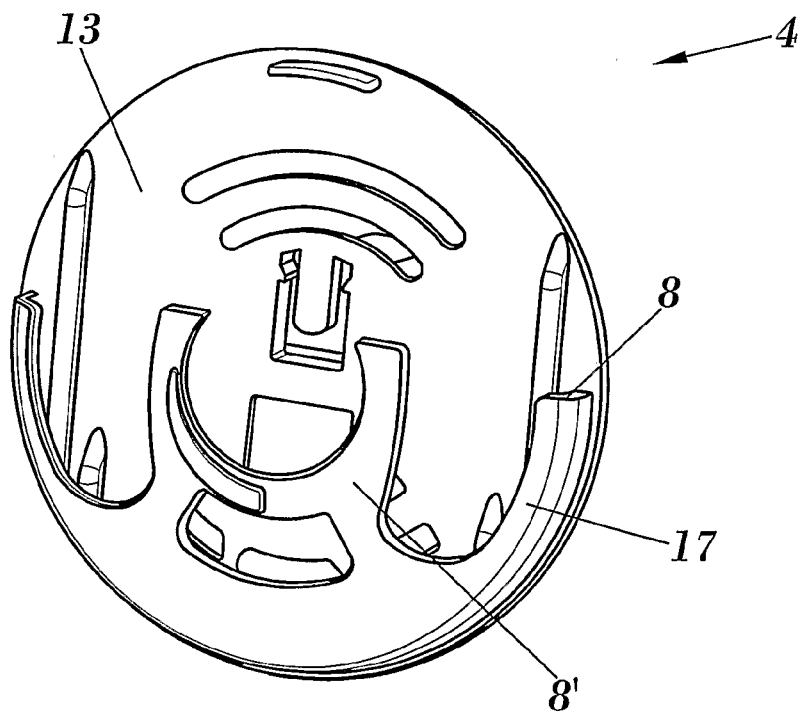
Figure 14A:
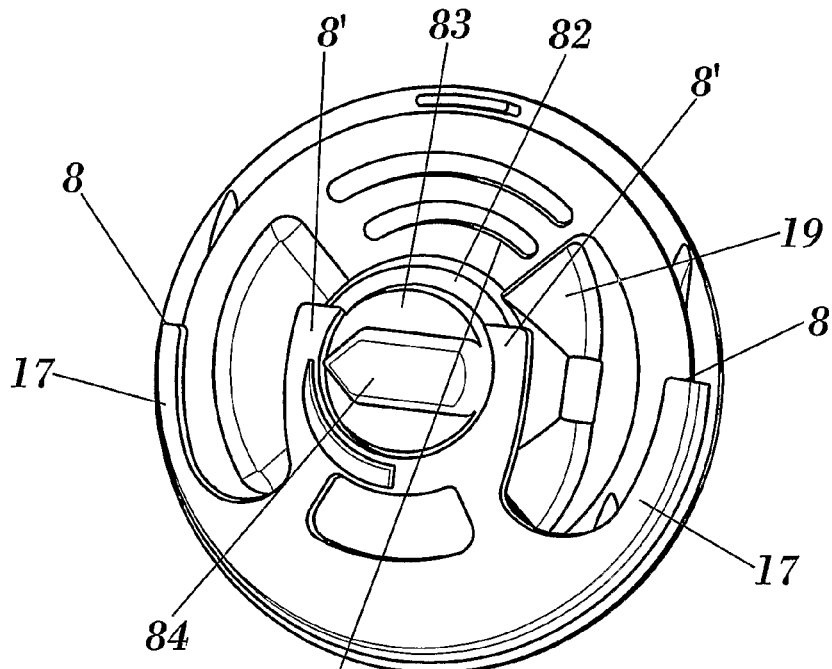
FIGS. 14A, 14B and 14C show views in different positions of the use of the device according to the fifth embodiment of the present invention. Thus, in FIG. 14A, the non-useful part of the container fully covers the holes in the housing.
Figure 14B:
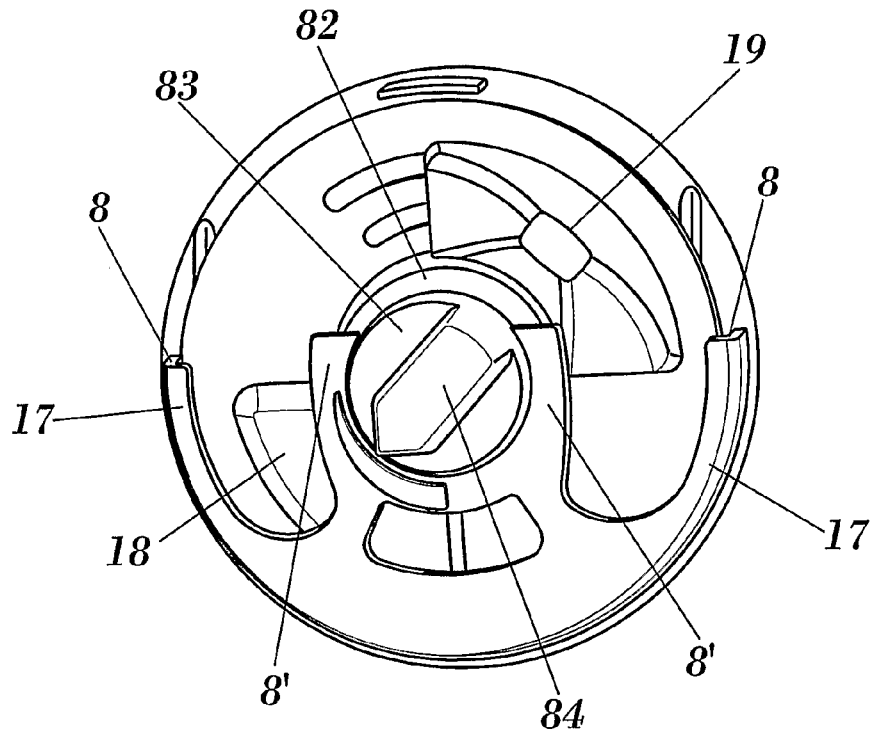
Figure 14C:
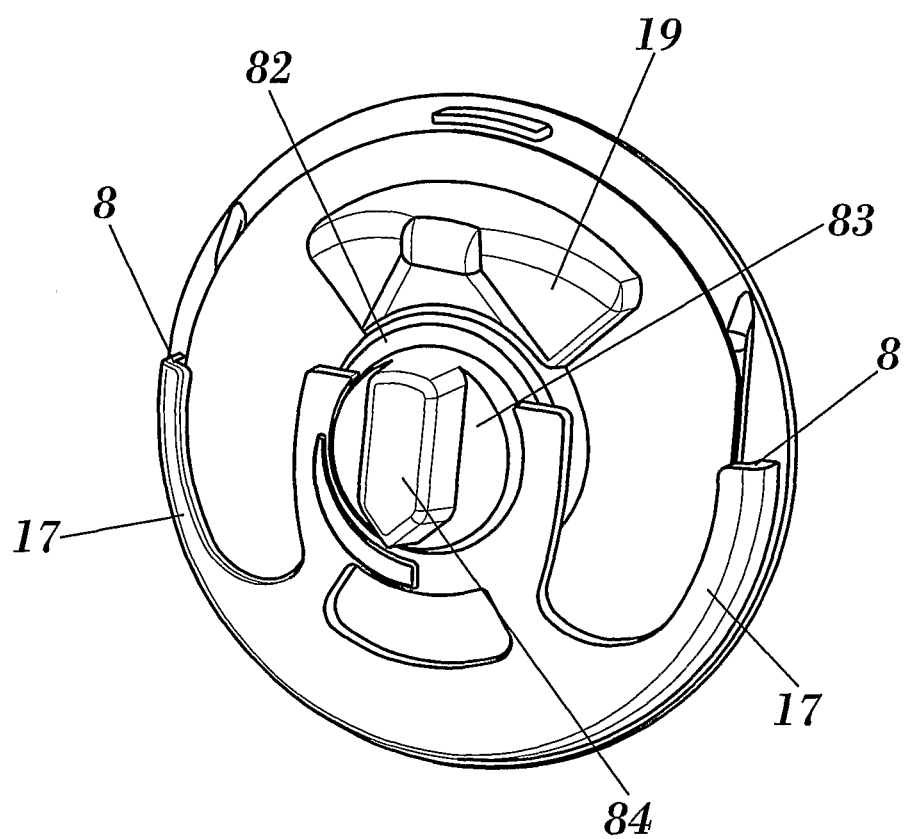

As in the previous embodiment, the housing (4) has at least one hole or opening (7) that communicates or communicate the outer wall (14) of the housing (4) with the inner wall (13) of said housing (4), which facilitates or facilitate the evaporation of said volatile substance, the degree of the evaporation of the volatile substance being regulated according to the greater or lesser extent to which the semipermeable membrane (3) adhered to the container (2) is aligned with said hole or holes (7). This is shown in FIGS. 14A, 14B and 14C. If the housing (4) has various holes or openings (7), these are grouped into at least one selected area of the housing (4) and the device may be designed so that the openings or holes (7) are grouped in various selected areas of the housing (4). This is shown in FIGS. 13A and 13B, in which the holes or openings (7), which in this case have the form of slots, are grouped in two selected areas of the housing. In this case the two areas, each of which has one group of openings or holes (7) are opposed in respect of the centreline dividing the housing into two semicircumferences, but said groups of holes or openings (7) may be arranged in a different way in the housing (4).

Figure 12A:
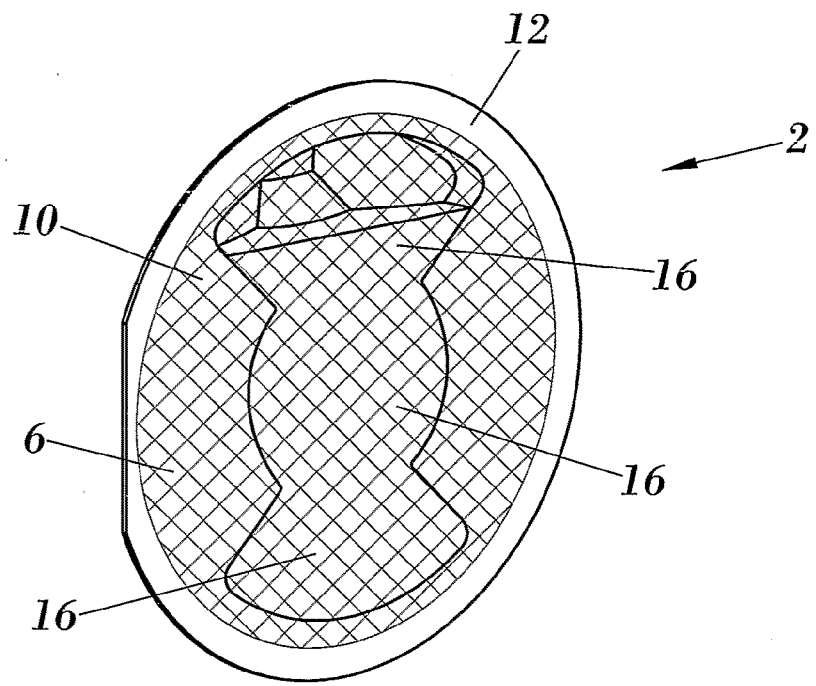
FIGS. 12A and 12B show rear and front views of the container, according to the fifth embodiment of the present invention.
Figure 12B:
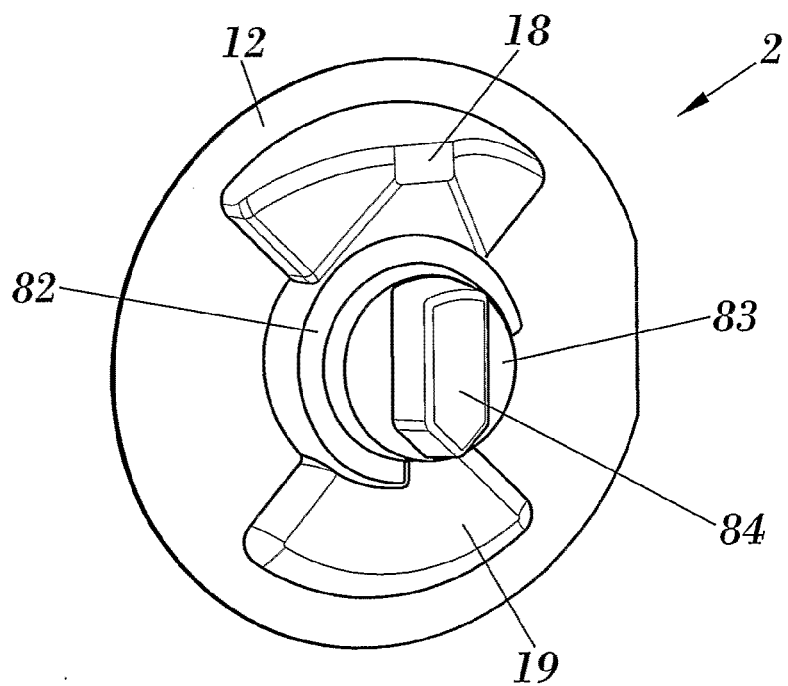

Similarly to the fourth embodiment, as is shown in FIG. 12A, on its face closed by the semipermeable membrane, the container (2) comprises a useful part (16) in contact with the volatile substance and a non-useful part (6) isolated from the volatile substance, the extent of the evaporation of said volatile substance being regulated according to whether the opening or hole or openings or holes (7) in the housing (4) are aligned partly or entirely with said non-useful part (6) of the face (10) of the container (2). This is observed in FIGS. 14A, 14B and 14C. In other words, the degree of evaporation of the volatile substance is regulated according to whether the openings or holes (7) in the housing (4) are aligned partly or entirely with said useful part (16) in contact with the volatile substance.

The holes or openings (7) in the housing (4) may be made by the methods familiar to experts on the matter. If the housing (4) has a single hole or opening (7), this may adopt a larger diameter than that of the case of various holes in order to permit good adjustment of the evaporation of volatile substance in the case of maximum regulation.

As shown by FIGS. 11B and 12B, in this fifth embodiment of the present invention, the useful part (16) comprises a first receptacle, chamber or cavity (18) connected or linked to a second receptacle, cavity or chamber (82) situated in the central portion of the container (2), and a third receptacle, cavity or chamber (19), opposite the first receptacle, chamber or cavity (18). The second receptacle, cavity or chamber (82) situated in the central portion of the container (2) communicates or links the first receptacle (18) with the third one (19). As may be seen in FIGS. 11B and 12B, the first (18) and third (19) receptacle are in two selected areas of the container (2). In this case, the two receptacles (18, 19) are opposed in respect of the centreline dividing the semipermeable membrane (3) into two semicircumferences, but said receptacles (18, 19) could be arranged in a different way in the container (2). On its outer side the second receptacle (82) comprises a protuberance or lesser receptacle (83) of smaller size than the rest of said second receptacle (82), in such a way that the turning of this protuberance brings about the guiding movement of the container (2) in respect of the housing (4). Put in another way, this protuberance or lesser receptacle (83) is a subcavity that extends the second cavity or receptacle (82). This protuberance or lesser receptacle (83) is capped at the top by a final element (84), which may be solid (i.e. not house volatile substance) or hollow (i.e. houses volatile substance). This last element (84), preferably of smaller size than the protuberance (83) from which it stems, may be a die, a cylinder, a button, a cone, a nut or any other equivalent or similar element.

During the operation of the device (1), the protuberance or lesser receptacle (83) of the second receptacle (82) of the container (2) engages with the other guiding means (8') situated in the central portion of the inner wall (13) of the housing (4), in such a way that the guided movement of the container (2) in respect of the housing (4) is doubly assisted by this engagement of the guiding means (8') with the protuberance (83).

This last element (84) capping the protuberance (83) of the second receptacle (82) also provides the advantage that it permits and facilitates the handling of the device by the user. Thus, for example, this element (84) facilitates the support of the fingers in order to facilitate the turning of the container (2). Furthermore, the protuberance (83) together with the element (84) endows the device with greater strength against front pressures.

Preferably, the two parts, the useful one (6) and the non-useful one (16) of the container (2) form a single structure, preferably of plastic material, which may be PET, PP, PVC or others.

As in the fourth embodiment, in an alternative to this fifth embodiment, not shown in the figures accompanying this description, the non-useful part (6) of the container (2) encompasses or comprises only the perimeter of the useful part (16), said non-useful part (6) forming a flat lip on which the semipermeable membrane (3) and the container (2) are joined. That is to say, in this case, the non-useful part (6) of the container (2) is that physically necessary to join the semipermeable membrane (3) and the container (2). This joint between the semipermeable membrane (3) and the container (2) on this flat peripheral lip is preferably welded. In this case, the surface area of the face (10) closed by the semipermeable membrane (3) is substantially smaller than the surface area of the inner wall (13) of the housing (4), as the rest of the non-useful part (6) has been trimmed or die-stamped, i.e. it has been removed, limiting said non-useful part (6) to the minimum necessary (said peripheral lip) to join or weld the semipermeable membrane (3). In this case, the useful part (16) may also define one or more cavities or receptacles, and one of these, preferably the receptacle which is situated in the central portion of the container (2), may also comprise, in its outer portion, a protuberance or lesser receptacle (83) which engages with the other guiding means (8') situated in the central portion of the inner wall (13) of the housing (4), in such a way that the turning of this protuberance (83) brings about and facilitates the guiding movement of the container (2) in respect of the housing (4). This protuberance or lesser receptacle (83) may be capped at the top by a final element (84), which may be solid (i.e. not house volatile substance) or hollow (i.e. houses volatile substance). This last element (84), preferably of smaller size than the protuberance (83) from which it stems, may be a die, a cylinder, a button, a cone, a nut or any other equivalent or similar element.

In all the possible embodiments of the present invention, not one but several cavities may be designed that house either the same volatile substance or several different volatile substances. The device may also be designed in such a way that the surface of the container that is in contact with the semipermeable membrane has different "non-useful" areas, i.e. different parts fully isolated from the volatile substances.

Figure 10:
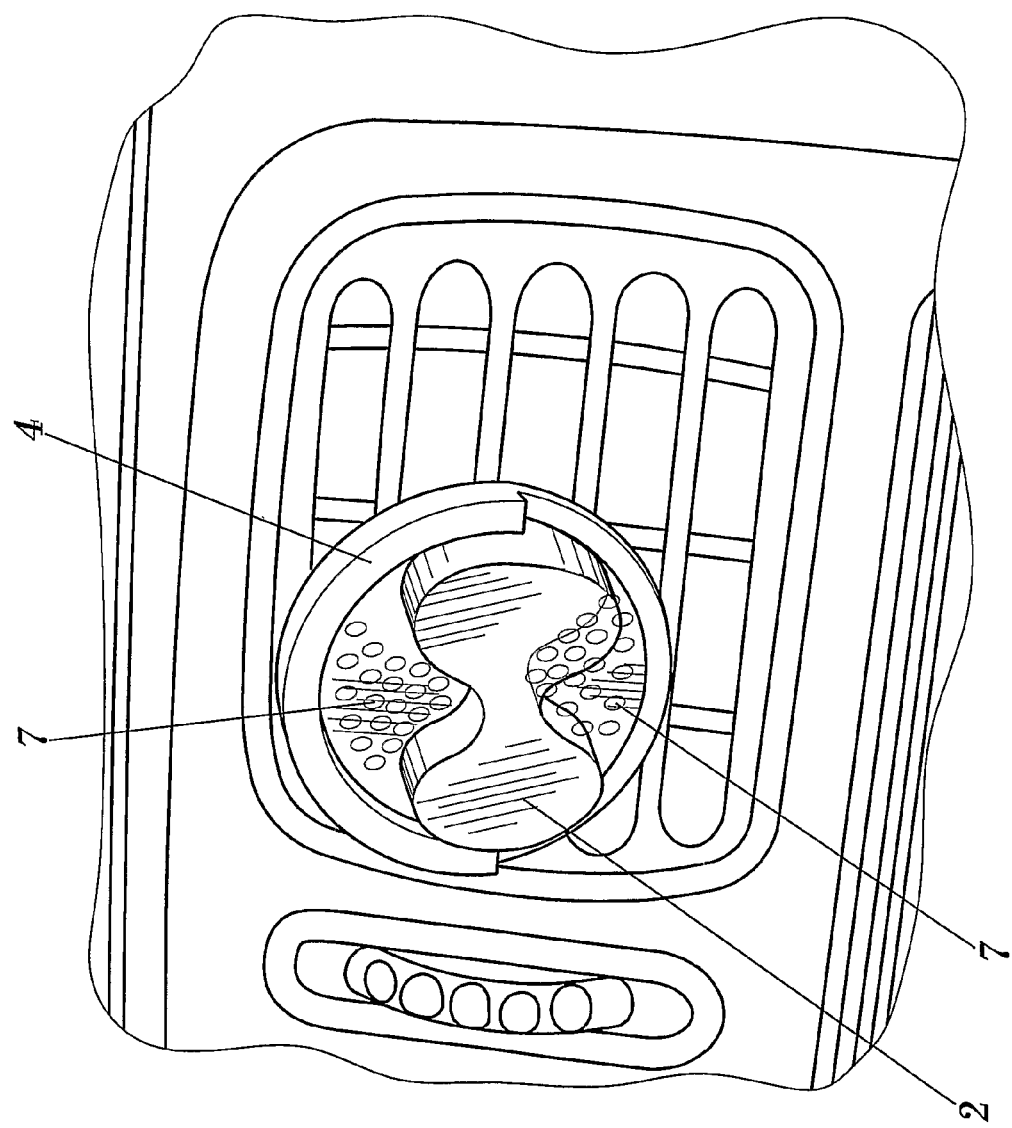
FIG. 10 shows a specimen use of the device, attached to the grille of a vehicle.

Both the housing and the container of any of the embodiments may adopt means of attachment or fixing to any environment. These fastening means may entail the fitting of an additional piece to the device; said piece, however, does not play a part in the functions of regulating the evaporation of the volatile matter, which is done with the sole action of the housing and the container. FIG. 11A shows an example of the inclusion of an additional piece as a means of fastening (81), incorporated in this case in the outer wall (14) of the housing (4). In this instance, said fastening element comprises a clip, but other fastening means (81), such as a hook, adhesive, or any other, are also possible. The environments to which the device may be fixed can be any component of a vehicle, any ventilation grille situated in any open or closed environment, on an air conditioning system or any other environment, in such a way that the device (1) is immersed in the air stream generated, part of which passes through said device. However, the device does not need to be immersed under the influence of a stream of forced air. FIG. 10 illustrates one of these possibilities.

In all the possible embodiments of the present invention, the device may incorporate other ancillary parts, such as a cover, box or other housing for cosmetic or other purposes. Said ancillary parts play no part in the process of controlling the evaporation of the volatile matter, which is carried out with the sole intervention of the housing and the container, as we have explained in the course of this description.

To enhance the appearance of the device (1), the container (2) may be transparent and the volatile substance contained in it may be coloured, for example with a colour that is associated with the aroma given off by said substance.

The device may be placed in any angular position. It may also be attached both to a vertical and to a horizontal grille, without its operation being affected.

In the possible embodiments of the invention described, it may be observed that on the device the semipermeable membrane takes on a layout transverse to the direction of the forward movement of the air flow. However, in other possible embodiments said layout of the semipermeable membrane could present a certain inclination in relation to the air flow.

In the light of this description and set of figures, experts on the matter could appreciate that the invention has been described according to some preferred embodiments of same, but that countless variations may be introduced into said preferred embodiments, without departing from the scope of the invention as claimed.

The invention claimed is:

1. Volatile substance evaporating device (1, 21, 41, 61) with the degree of evaporation adjustable, which comprises:
   a container (2, 22, 42, 62) that has at least one cavity (5, 25, 45, 65) which houses a volatile substance;
   a semipermeable membrane (3, 23, 43, 63), adhered to the container (2, 22, 42, 62), which closes one of the faces (10, 30, 50, 70) of said container (2, 22, 42, 62) and which is at least partly in contact with the volatile substance housed in said cavity (5, 25, 45, 65);
   a housing (4, 24, 44, 64) which comprises at least an outer wall (14, 34, 54, 74) and an inner wall (13, 33, 53, 73);
   guiding means (8, 48, 68) that permit the relative movement between the housing (4, 44, 64) and the container (2, 42, 62);
   characterised in that
   the container (2, 22, 42, 62) and the housing (4, 24, 44, 64) are coupled directly to each other, either partly or entirely, on the same plane, by the face (10, 30, 50, 70) of the container (2, 22, 42, 62) closed by the semipermeable membrane (3, 23, 43, 63) and by the inner wall (13, 33, 53, 73) of the housing (4, 24, 44, 64),
   and in that the container (2, 22, 42, 62) and the housing (4, 24, 44, 64) are movable in respect of each other, the degree of evaporation of the volatile substance being regulated by the relative movement between the housing (4, 24, 44, 64) and the container (2, 22, 42, 62);
   further characterised in that
   the degree of evaporation of said volatile substance is determined by the amount of surface area of the inner wall (53, 73) of the housing (44, 64) which is coupled directly to the container (42, 62), on its face (50, 70) closed by the semipermeable membrane (43, 63).

2. Device according to claim 1, characterised by means of articulation (9) that permit the relative movement between the housing (24) and the container (22).

3. Device according to claim 2, further characterised in that the degree of evaporation of said volatile substance is determined by the amount of the surface area of the inner wall (33) of the housing (24) which is coupled directly to a certain amount of semipermeable membrane (23), said degree of evaporation being minimum when the whole of the surface area of the semipermeable membrane (23) is hidden by the inner wall (33) of the housing (24) and maximum when the semipermeable membrane (23) is completely uncovered by the inner wall (33) of the housing (24).

4. Device according to claim 1, further characterised in that, on its face (10) closed by the semipermeable membrane (3), the container (2) is coupled entirely on the inner wall (13) of the housing (4).

5. Device according to claim 1, further characterised in that the dimensions of the inner wall (53) of the housing (44) are similar to those of the semipermeable membrane (43), the degree of evaporation being minimum when the whole of the surface area of the semipermeable membrane (43) is hidden by the inner wall (53) of the housing (44) and maximum when the semipermeable membrane (43) is entirely uncovered by the inner wall (53) of the housing (44).

6. Device according to claim 1, characterised in that the height of the inner wall (73) of the housing (64) is considerably higher than the height of the cavity (65) housing the volatile substance.

7. Device according to claim 6, characterised in that the housing (64) has at least one hole or opening (67) that communicates the outer wall (74) of the housing (64) with the inner wall (73) of said housing (64), which facilitates the evaporation of said volatile substance, the degree of the evaporation of the volatile substance being regulated by means of the extent to which the semipermeable membrane (63) is aligned with at least one of the said holes or openings (67) in the housing (64).

8. Device according to claim 7, characterised in that the housing (64) has at least one cluster of holes or openings (67) that communicate the outer wall (74) of the housing (64) with the inner wall (73) of said housing (64), in a selected area of said housing (64).

9. Device according to claim 4, characterised in that the housing (4) has at least one hole or opening (7) that communicates the outer wall (14) of the housing (4) with the inner wall (13) of said housing (4), said at least one hole or opening (7) facilitating the evaporation of said volatile substance, the degree of the evaporation of the volatile substance being regulated by means of the greater or lesser extent to which the semipermeable membrane (3) is aligned with the at least one hole or opening (7) in the housing (4).

10. Device according to claim 9, characterised in that the housing (4) has at least a cluster of holes or openings (7) that communicate the outer wall (14) of the housing (4) with the inner wall (13) of said housing (4), in a selected area of said housing (4).

11. Device according to claim 9 or 10, characterised in that, on its face (10) closed by the semipermeable membrane (3) the container (2) comprises a useful part (16), which defines the cavity (5), in contact with the volatile substance, and a non-useful part (6) isolated from the volatile substance, the degree of the evaporation of said volatile substance being regulated according to whether the opening(s) or hole(s) (7) in the housing (4) are aligned partly or fully with said useful part (16) of the container (2).

12. Device according to claim 11, characterised in that the non-useful part (6) of the container (2) takes on the form of a laminar surface.

13. Device according to claim 12, characterised in that the part of the semipermeable membrane (3) that is adhered to the non-useful part (6) in the form of a laminar surface of the container (2) is joined entirely to said non-useful part (6) in the form of a laminar surface of the container (2).

14. Device according to claim 13, characterised in that the said joint between the non-useful part (6) in the form of a laminar surface of the container (2) and the semipermeable membrane (3) is welded.

15. Device according to claim 12, characterised in that the non-useful part (6) comprises only the perimeter of the useful part (16), said non-useful part (6) forming a flat lip on which the semipermeable membrane (3) and the container (2) are joint.

16. Device according to claim 11, characterised in that the non-useful part (6) of the container (2) defines a second cavity completely separate from the cavity (5) in which the volatile substance is housed, said separation being achieved by means of a weld zone between the semipermeable membrane (3) and the container (2).

17. Device according to claim 11, characterised in that the non-useful part (6) of the container (2) comprises a hole.

18. Device according to any of the claims 11 to 17, characterised in that the cavity (5) of the container (2) defined by the useful part (16) comprises at least two receptacles (18, 19) linked to each other by a channel (20) which is narrower than the at least two receptacles (18, 19).

19. Device according to any of the claims 11 to 17, characterised in that the cavity (5) of the container (2) defined by the useful part (16) comprises at least one receptacle (18) linked to a second receptacle (82) situated in the central portion of the container (2).

20. Device according to claim 19, characterised in that the cavity (5) of the container (2) defined by the useful part (16) comprises at least a third receptacle (19), the first receptacle (18) and the third receptacle (19) being linked by means of the second receptacle (82) situated in the central portion of the container (2).

21. Device according to either of claim 19 or 20, characterised in that said second receptacle (82) comprises on its outer side a protuberance or lesser receptacle (83), of smaller size than the rest of said second receptacle (82).

22. Device according to claim 21, characterised in that said protuberance or lesser receptacle (83) comprises on its outer side an element (84) of smaller size than said protuberance or lesser receptacle (83).

23. Device according to claim 22, characterised in that said element (84) is solid, i.e. does not house volatile substance in its interior.

24. Device according to claim 22, characterised in that said element (84) is hollow, i.e. houses volatile substance in its interior.

25. Device according to any of claim 21, 22, 23 or 24, characterised in that the housing (4) also comprises other guiding means (8'), situated in the central portion of said housing (4), to which the protuberance or lesser receptacle (83) of the second receptacle (82) of the container (2) is coupled.

26. Device according to claim 15, characterised in that the surface area of the face (10) closed by the semipermeable membrane (3) is substantially smaller than the surface area of the inner wall (13) of the housing (4).

27. Device according to any of the preceding claims, further characterised in that the container (2, 22, 42, 62) is movable in respect of the housing (4, 24, 44, 64), which remains fixed.

28. Device according to any of the preceding claims, further characterised in that the housing (4, 24, 44, 64) is movable in respect of the container (2, 22, 42, 62), which remains fixed.

29. Device according to any of the preceding claims, characterised in that the semipermeable membrane (3, 23, 43, 63) fits snugly to the inner wall (13, 33, 53, 73) of the housing (4, 24, 44, 64) when the container (2, 22, 42, 62) and the housing (4, 24, 44, 64) are entirely or partly coupled.

30. Device according to any of the preceding claims, characterised in that the semipermeable membrane (3, 23, 43, 63) is slightly separated from the inner wall (13, 33, 53, 73) of the housing (4, 24, 44, 64) when the container (2, 22, 42, 62) and the housing (4, 24, 44, 64) are entirely or partly coupled.

31. Device according to any of the preceding claims, characterised in that the housing (4, 24, 44, 64) is made of one single piece.

32. Device according to claim 31, characterised in that said piece is a plastic material structure produced by means of injection moulding.

33. Device according to claim 31 or 32, characterised in that said piece is rigid.

34. Device according to any of the preceding claims, characterised in that the container (2, 22, 42, 62) adopts a form that makes for its easy handling.

35. Device according to any of the preceding claims, characterised in that the housing (4, 24, 44, 64) has fastening means for fastening in any environment.

36. Device according to any of the preceding claims, characterised in that the container (2, 22, 42, 62) is made of a single piece.

37. Device according to any of the preceding claims, characterised by a protection strip adhered to the outer surface of the semipermeable membrane (3, 23, 43, 63), said protection strip being intended to prevent the evaporation of the volatile substance prior to the use of evaporator device (1, 21, 41, 61).

38. Device according to claim 27, characterised in that said protection strip extends partly from the device (1, 21, 41, 61) forming a tab which facilitates its removal.

39. Device according to any of the preceding claims, characterised in that the device (1, 21, 41, 61) is detachable, that is to say, the housing (4, 24, 44, 64) and the container (2, 22, 42, 62) can be taken apart in order to permit the fitting of a new container (2, 22, 42, 62) filled with volatile substance.

40. Device according to any of the preceding claims, characterised in that it incorporates at least another piece connected to the housing (4, 24, 44, 64) and/or the container (2, 22, 42, 62) which takes no part in regulating the degree of evaporation of the volatile substance.

* * * * *